US012599488B2

(12) United States Patent
Keem

(10) Patent No.: US 12,599,488 B2
(45) Date of Patent: Apr. 14, 2026

(54) BI-PLANAR EXPANDABLE CAGE FOR SPINE

(71) Applicant: HILO INNOVATIONS, LLC, Wilmington, DE (US)

(72) Inventor: Sean Kyong-Ho Keem, Santa Barbara, CA (US)

(73) Assignee: HILO INNOVATIONS, LLC, Wilmington, DE (US)

( * ) Notice: Subject to any disclaimer, the term of this patent is extended or adjusted under 35 U.S.C. 154(b) by 0 days.

(21) Appl. No.: 18/770,189

(22) Filed: Jul. 11, 2024

(65) Prior Publication Data

US 2024/0366400 A1     Nov. 7, 2024

Related U.S. Application Data

(63) Continuation of application No. PCT/IB2022/060509, filed on Nov. 1, 2022, which is a continuation of application No. PCT/IB2022/051270, filed on Feb. 14, 2022.

(51) Int. Cl.
     A61F 2/44          (2006.01)
     A61F 2/30          (2006.01)
(52) U.S. Cl.
     CPC .... A61F 2/447 (2013.01); *A61F 2002/30433* (2013.01)
(58) Field of Classification Search
     CPC ........................... A61F 2/447; A61F 2002/443
     See application file for complete search history.

(56) References Cited

U.S. PATENT DOCUMENTS

| | | | | |
|---|---|---|---|---|
| 10,398,563 B2 * | 9/2019 | Engstrom | ............... | A61F 2/442 |
| 10,687,963 B2 * | 6/2020 | Jimenez | .................. | A61F 2/447 |
| 11,399,959 B2 * | 8/2022 | Keem | ................... | A61F 2/4455 |
| 11,517,443 B2 * | 12/2022 | Dewey | ................. | A61F 2/4425 |

(Continued)

FOREIGN PATENT DOCUMENTS

| | | |
|---|---|---|
| EP | 3939548 A1 | 1/2022 |
| JP | 2019-520156 A | 7/2019 |

(Continued)

OTHER PUBLICATIONS

Keem, Sean Kyong Ho, KR 10-2192022, Dec. 16, 2020, English Translation Generated Aug. 12, 2025. (Year: 2020).*

*Primary Examiner* — Eduardo C Robert
(74) *Attorney, Agent, or Firm* — Bridgeway IP Law Group, PLLC; Sang Ho Lee; Hyun Woo Shin

(57)          ABSTRACT

An expandable cage for a spine includes an upper structural body, a lower structural body, a main frame having control mechanism insertion holes defined through one side and the other side in the longitudinal direction thereof, respectively, a sagittal balance control unit coupled to one side of each of the upper structural body and the lower structural body to control a sagittal balance of a spine by adjusting a spacing distance between the upper structural body and the lower structural body, and a coronal balance control unit coupled to the other side of each of the upper structural body and the lower structural body to control a coronal balance of a spine by controlling a gradient of the upper structural body and the lower structural body by lifting or lowering the other side of each of the upper structural body and the lower structural body.

7 Claims, 20 Drawing Sheets

(56)                    References Cited

U.S. PATENT DOCUMENTS

| | | | |
|---|---|---|---|
| 11,963,881 B2 * | 4/2024 | Josse ..................... | A61F 2/4611 |
| 12,318,308 B2 * | 6/2025 | Josse ................... | A61F 2/30749 |
| 2005/0182416 A1 | 8/2005 | Lim et al. | |
| 2019/0274837 A1 * | 9/2019 | Eisen .................... | A61F 2/4611 |
| 2019/0336301 A1 | 11/2019 | Engstrom | |
| 2020/0281741 A1 * | 9/2020 | Grotz ..................... | A61F 2/447 |
| 2021/0077272 A1 | 3/2021 | Eisen et al. | |
| 2021/0378832 A1 * | 12/2021 | Altarac .................. | A61F 2/447 |

FOREIGN PATENT DOCUMENTS

| | | |
|---|---|---|
| JP | 2021-517015 A | 7/2021 |
| KR | 10-1352820 A | 1/2014 |
| KR | 10-1552476 B1 | 9/2015 |
| KR | 10-2017-0118056 A | 10/2017 |
| KR | 10-2032786 B1 | 10/2019 |
| KR | 10-2020-0011636 A | 2/2020 |
| KR | 10-2103833 B1 | 4/2020 |
| KR | 10-2192022 B1 | 12/2020 |

* cited by examiner

BI-PLANAR EXPANDABLE CAGE FOR SPINE

CROSS-REFERENCE TO RELATED APPLICATION

This application is a continuation application of International Application No. PCT/IB2022/060509, filed on Nov. 1, 2022, which claims priority to International Application No. PCT/IB2022/051270, filed on Feb. 14, 2022, in the International Bureau, the entire disclosures of which are incorporated herein by reference.

TECHNICAL FIELD

The present disclosure relates to an expandable cage for a spine, and more specifically, to an expandable cage for a spine which secures a gap between vertebral bodies by replacing a damaged disc between spinal vertebrae to treat diseases related to spinal discs, thereby restoring the spinal function.

BACKGROUND ART

In general, the discs between the spinal vertebrae, excluding first and second cervical vertebrae, absorb the load and shock of the body, act as a buffer to distribute impact like a cushion, prevent the vertebrae from dislocating, provide an appropriate stance by keeping the two vertebrae apart so that the spinal nerves are not compressed, and aid in the smooth movement of each vertebra.

Meanwhile, the discs, due to injuries, aging or abnormal posture maintained over a long period, may become degenerated, leading to various associated negative effects, such as the gradual narrowing of the space between the spines or the deformity of the vertebrae, resulting in instability and imbalance in spinal alignments.

As a method for treating such diseases associated with the disc degeneration, spinal arthrodesis (fusion), which involves removing the damaged disc between the vertebrae and inserting a prosthetic material, intervertebral prosthesis, commonly known as a cage, into the space between the two adjacent vertebrae to replace the disc, has been used. The cage plays a significant role in restoring the pre-morbid distance between the vertebrae, thereby recovering the spinal function.

As an example of the technology related to such cage, Korean Patent No. 10-1352820 discloses an expansion cage between vertebral bodies, which comprises: a cage body including an upper support part located above between the vertebral bodies to support the vertebral body, a lower support part located below between the vertebral bodies to support the vertebral body, and a connection part connecting the ends of the upper and lower support parts; and a sliding member which moves slidingly between the upper and lower support parts to widen or narrow the gap between the upper and lower support parts, wherein the sliding member includes a pressure bolt, which is screw-coupled to the sliding member to allow the sliding member slide.

Meanwhile, in fact, spinal deformities such as scoliosis and kyphosis often do not present alone but as complex deformities where scoliosis and kyphosis occur concurrently in a three-dimensional plane.

However, a conventional expandable cage for a spine is designed to correct either the sagittal balance or the coronal balance of the spine only. Since most spinal deformities occur in a three-dimension, the conventional cage has limited therapeutic effectiveness and is inadequate for treating the spine with complex deformities.

Furthermore, the conventional expandable cages are often introduced from the back of the spine, risking injury to the nerves, muscles and ligaments of the human body during insertion process, thus increasing the burden of treatment. There is a critical need for the development of expandable cages for the spine capable of addressing the above-mentioned issues.

DISCLOSURE

Technical Problem

Accordingly, the present invention has been made in view of the above-mentioned problems occurring in the related art, and it is an object of the present invention to provide an expandable cage for a spine, which can adjust not only the sagittal balance but also the coronal balance of the spine, thereby enabling effective treatment of the spine with complex deformities using a single expandable cage.

It is another object of the present invention to provide an expandable cage for a spine, which is designed for insertion via lateral approach (trans-psoas approach) or anterolateral approach (ante-psoas approach), thereby reducing potential neurological injury and post-operative pain arising from cutting muscles or ligaments needed for posterior or posterolateral approaches.

In addition, the insertion method of the expandable cage for a spine of the present invention can be adapted not only for insertion from either side of the spine, but also an anterior insertion (ALIF) or a posterior insertion (TLIF or PLIF) depending on the surgical method, anatomical limitations, and desired deformity correction location.

Technical Solution

To accomplish the above stated objects, an expandable cage for a spine includes: an upper structural body; a lower structural body spaced at a predetermined distance below the upper structural body; a main frame provided between the upper and lower structural bodies, and having control mechanism insertion holes formed on both sides thereof in the longitudinal direction for insertion of a control mechanism; a sagittal balance control unit coupled to the main frame and coupled to one side of each of the upper and lower structural bodies to adjust the distance between the upper and lower structural bodies by the control mechanism inserted into the control mechanism insertion holes, thereby adjusting the sagittal balance of the spine; and a coronal balance control unit coupled to the main frame and coupled to the other side of each of the upper and lower structural bodies to adjust the inclination of the upper and lower structural bodies by elevating and lowering the other sides of the upper and lower structural bodies by the control mechanism inserted into the control mechanism insertion holes, thereby adjusting the coronal balance of the spine.

Moreover, the sagittal balance control unit includes: a height adjusting screw, arranged in the longitudinal direction of the upper and lower structural bodies, having a screw thread formed on the outer circumferential surface thereof, and rotating in conjunction with the rotation of the control mechanism which is inserted into the height adjusting screw; a height adjusting member, having a screw hole coaxial with the control mechanism insertion hole, and screw-coupled with the height adjusting screw to move according to the rotation of the height adjusting screw; and a height adjusting link, of which the upper end is to the upper structural body and the lower end is connected to the lower structural body, and which is linked with the height adjusting member to adjust the height between the upper and lower structural bodies according to the movement of the height adjusting member.

Furthermore, the height adjusting link includes: a fixed shaft coupled to the main frame; a moving shaft provided on the height adjusting member; a first height adjusting link frame, of which one side is rotatably coupled to the fixed shaft and the other side is rotatably coupled to the upper structural body; a second height adjusting link frame, of which one side is rotatably coupled to the fixed shaft and the other side is rotatably coupled to the lower structural body; a third height adjusting link frame, of which one side is rotatably coupled to the moving shaft and the other side is rotatably coupled to the upper structural body; and a fourth height adjusting link frame, of which one side is rotatably coupled to the moving shaft and the other side is rotatably coupled to the lower structural body, wherein the height adjusting link has a rhomboidal link structure such that the height between the upper and lower structural bodies is adjusted due to the distance between the moving shaft and the fixed shaft.

Additionally, the coronal balance control unit includes: an inclination adjusting screw, arranged in the longitudinal direction of the upper and lower structural bodies, having a screw thread formed on the outer circumferential surface thereof, and rotating in conjunction with the rotation of the control mechanism which is inserted into the inclination adjusting screw; an inclination adjusting member, having a screw hole coaxial with the control mechanism insertion hole, and screw-coupled with the inclination adjusting screw to move according to the rotation of the inclination adjusting screw; and an inclination adjusting link, of which one side is to the upper structural body and the other side is connected to the lower structural body, and which adjusts the inclination between the upper and lower structural bodies according to the movement of the inclination adjusting member.

In addition, the inclination adjusting link includes: a rotational shaft provided on the inclination adjusting member; a first inclination adjusting link frame, of which one side is rotatably coupled to the rotational shaft and the other side is rotatably coupled to the upper structural body; and a second inclination adjusting link frame, of which one side is rotatably coupled to the rotational shaft and the other side is rotatably coupled to the lower structural body.

Moreover, the expandable cage further includes a guide member which is provided within the main frame to move freely, is formed to accommodate end portions of the height adjusting screw and the inclination adjusting screw, which are inserted in opposite directions to each other, thereby guiding both the height adjusting screw and the inclination adjusting screw.

Furthermore, the upper structural body includes a first fixing force forming part where the surface facing the upper vertebra is formed to protrude or to be recessed with a predetermined pattern to make fixation force between directly contacting parts, and the lower structural body comprises a second fixing force forming part where the surface facing the upper vertebra is formed to protrude or to be recessed with a predetermined pattern to make fixation force between directly contacting parts.

Additionally, the height adjusting screw comprises a first adjusting hole into which the control mechanism is inserted, and which is rotated by the rotation of the control mechanism and has a polygonal cross-sectional shape, and the inclination adjusting screw comprises a second adjusting hole into which the control mechanism is inserted, and which is rotated by the rotation of the control mechanism and has the same diameter and cross-sectional shape as the first adjusting hole.

In addition, the height adjusting screw is aligned with the inclination adjusting screw, such that the first adjusting hole and the second adjusting hole are coaxially arranged, and the control mechanism is configured to rotate at least one of the height adjusting screw or the inclination adjusting screw depending on the insertion depth.

Advantageous Effect

The expandable cage for the spine according to an embodiment of the present invention can adjust not only the sagittal balance but also the coronal balance of the spines through the sagittal balance control unit and the coronal balance control unit, thereby enabling treatment of scoliosis or kyphosis, and enabling effective treatment of complex spinal deformities with a single configuration.

Furthermore, the expandable cage for the spine according to an embodiment of the present invention, which is designed to be inserted from the lateral position or the anterolateral position, allows for safe surgery by minimizing the risk of damage to muscles or ligaments of the human body during surgery, and is applicable for lateral lumbar interbody fusion (LLIF) as well as oblique (ante-psoas) lateral interbody fusion (OLIF).

Additionally, the insertion method of the expandable cage for the spine can be adapted not only for insertion from either side of the spine (LLIF, OLIF), but also for insertion with anterior approach (ALIF) or posterior approach (TLIF or PLIF) of the spine depending on the surgical method, anatomical limitations, and desired deformity correction location.

In addition, the expandable cage for the spine according to an embodiment of the present invention is designed for a user to easily operate both the sagittal balance control unit and the coronal balance control unit through a single control mechanism, thereby greatly facilitating the adjustment of the sagittal balance and the coronal balance.

Moreover, the expandable cage for the spine according to an embodiment of the present invention has both sides symmetrically formed with respect to the longitudinal (insertion) direction, thereby allowing for easy adjustment of the expansion position in the anterior-posterior direction according to the expansion position on either the left or right side of the spine, when adjusting the coronal balance through the coronal balance control unit, and minimizing an incision area.

Furthermore, the expandable cage for the spine according to an embodiment of the present invention is configured to adjust the sagittal balance and the coronal balance depending on the thread pitch by rotating the height adjusting screw of the sagittal balance control unit and the inclination adjusting screw of the coronal balance control unit, thereby allowing for optimal treatment tailored to the condition of the spine through fine-tuning of expansion depending on the thread pitch, and enhancing usability only through rotation of the height adjusting screw and the inclination adjusting screw.

BEST MODE

Figure 1A:
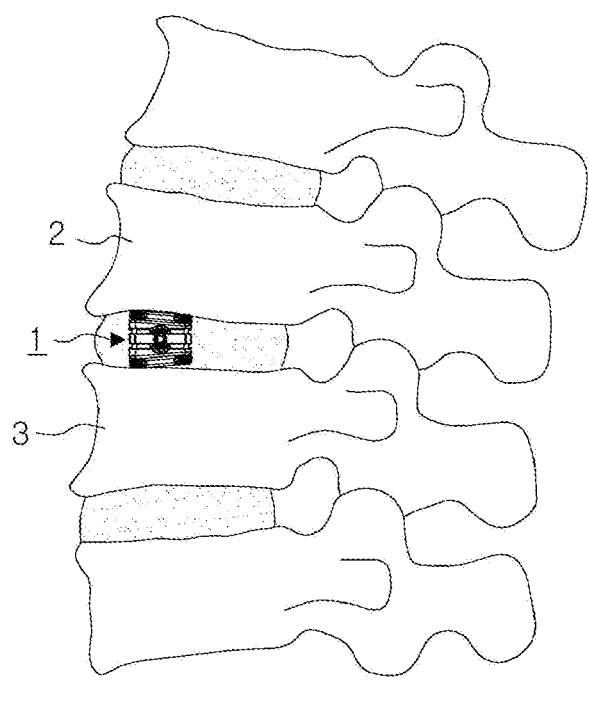
FIG. 1A is a view illustrating an expandable cage for a spine according to an embodiment of the present invention inserted into the spine, viewed from the sagittal plane of the spine.

An expandable cage for the spine according to an embodiment of the present invention includes: an upper structural body; a lower structural body spaced at a predetermined distance below the upper structural body; a main frame provided between the upper and lower structural bodies, and having control mechanism insertion holes formed on both sides thereof in the longitudinal direction for insertion of a control mechanism; a sagittal balance control unit coupled to the main frame and coupled to one side of each of the upper and lower structural bodies to adjust the distance between the upper and lower structural bodies by the control mechanism inserted into the control mechanism insertion holes, thereby adjusting the sagittal balance of the spine; and a coronal balance control unit coupled to the main frame and coupled to the other side of each of the upper and lower structural bodies to adjust the inclination of the upper and lower structural bodies by elevating and lowering the other sides of the upper and lower structural bodies by the control mechanism inserted into the control mechanism insertion holes, thereby adjusting the coronal balance of the spine.

MODE FOR INVENTION

Hereinafter, the description of the present invention with reference to the drawings is not limited to specific embodiments, and can undergo various modifications and have multiple embodiments. Additionally, it should be understood that the content described below encompasses all modifications, equivalents, or substitutes that fall within the spirit and technical scope of the present invention.

It will be understood that terms, such as "first" or "second" may be used in the specification to describe various components but are not restricted to the above terms. The terms may be used to discriminate one component from another component.

It will be further understood that the singular form of the components used in the present invention may be understood into the plural form unless otherwise specifically stated in the context. It should be also understood that the terms of 'include' or 'have' in the specification are used to mean that there are characteristics, numbers, steps, operations, components, parts, or combinations of the steps, operations, components and parts described in the specification and there is no intent to exclude existence or possibility of other characteristics, numbers, steps, operations, components, parts, or combinations of the steps, operations, components and parts.

Unless defined otherwise, it will be understood that all terms used in the specification including technical or scientific terms have the same meanings as to be generally or commonly understood by those of ordinary skill in the art. It will be further understood that words or terms described as the meaning defined in commonly used dictionaries shall be interpreted as having meanings that are consistent with their meanings in the context of the relevant art and the technical idea of the invention, and shall not be interpreted as having ideal meanings or excessively formal meanings, not otherwise particularly stated.

Moreover, in describing the invention with reference to the accompanying drawings, like elements are referenced by like reference numerals or signs regardless of the drawing numbers and description thereof is not repeated. In the description, details of well-known features and techniques may be omitted to avoid unnecessarily obscuring the presented embodiments.

Hereinafter, an expandable cage 1 for a spine according to an embodiment of the present invention will be described in detail with reference to the attached FIGS. 1 through 23B.

Figure 1B:
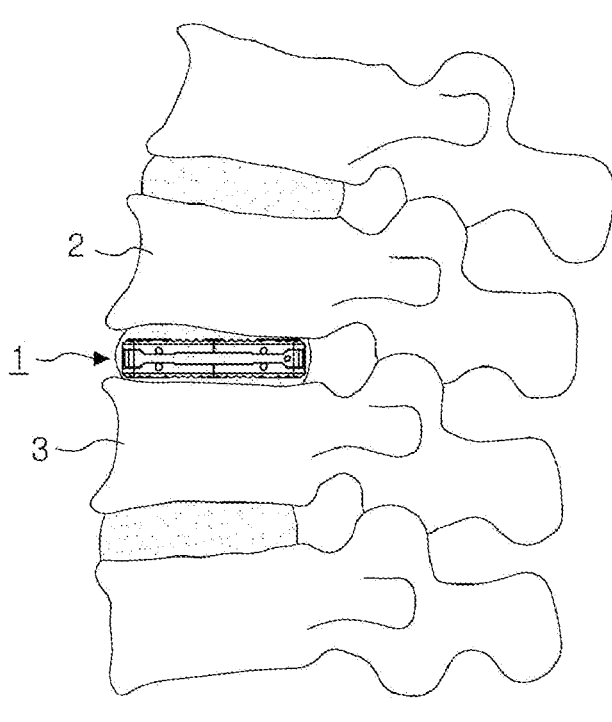
FIG. 1B is a view illustrating the expandable cage of FIG. 1A inserted into the spine in a different direction, viewed from the sagittal plane of the spine.
Figure 2:
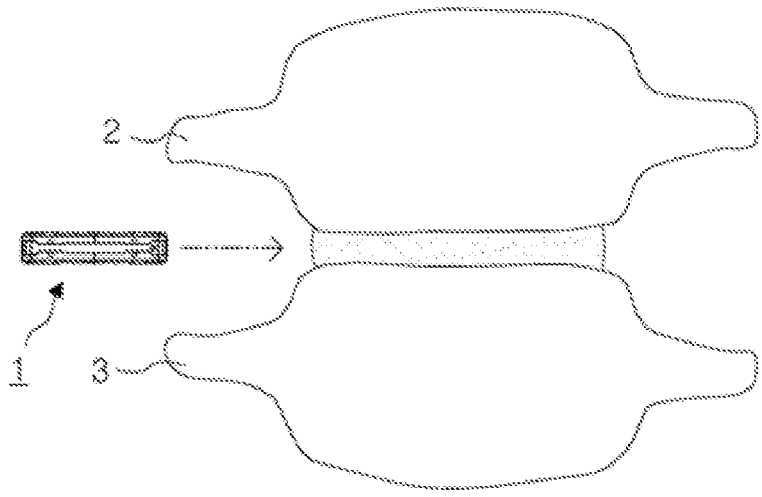
FIG. 2 is an illustrative view of the expandable cage inserted from the right side of the spine.
Figure 3:
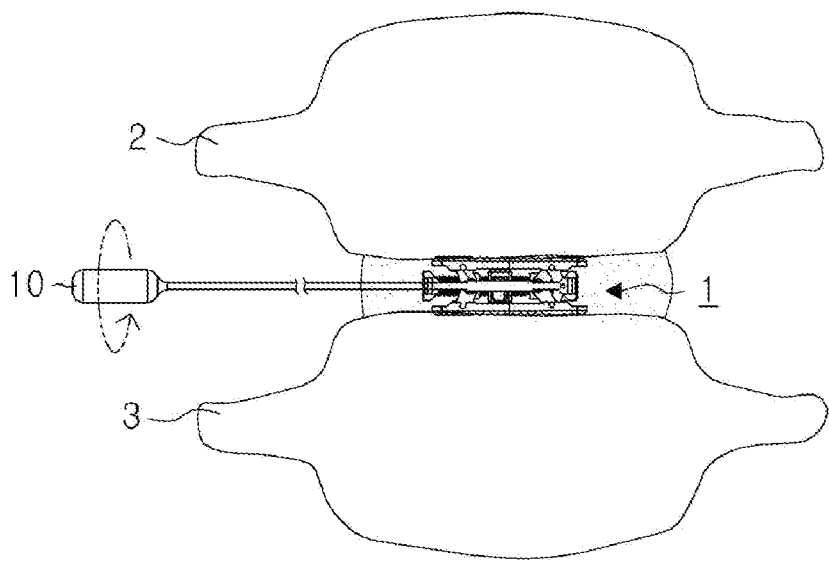
FIG. 3 is an operational view illustrating the adjustment of the sagittal balance of the spine after the insertion of the expandable cage for the spine.
Figure 4A:
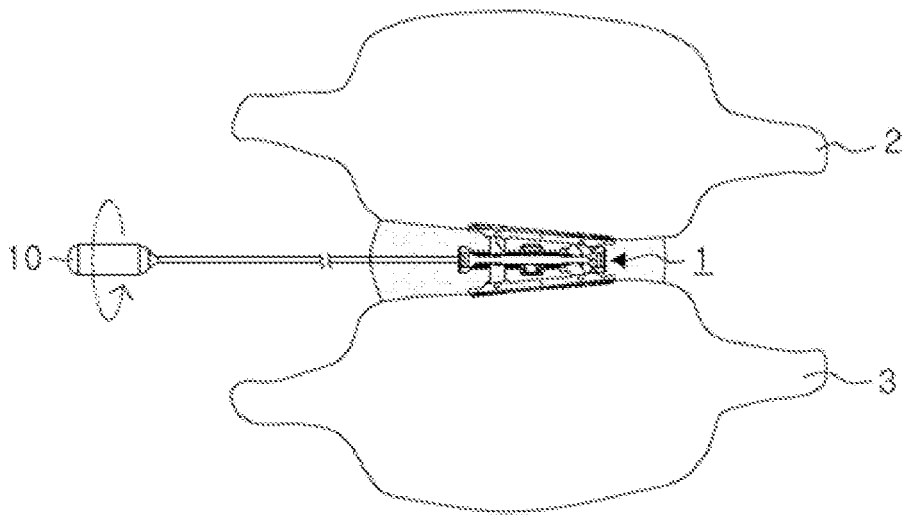
FIGS. 4A and 4B are operational view illustrating the adjustment of the coronal balance of the spine after the insertion of the expandable cage for the spine.
Figure 4B:
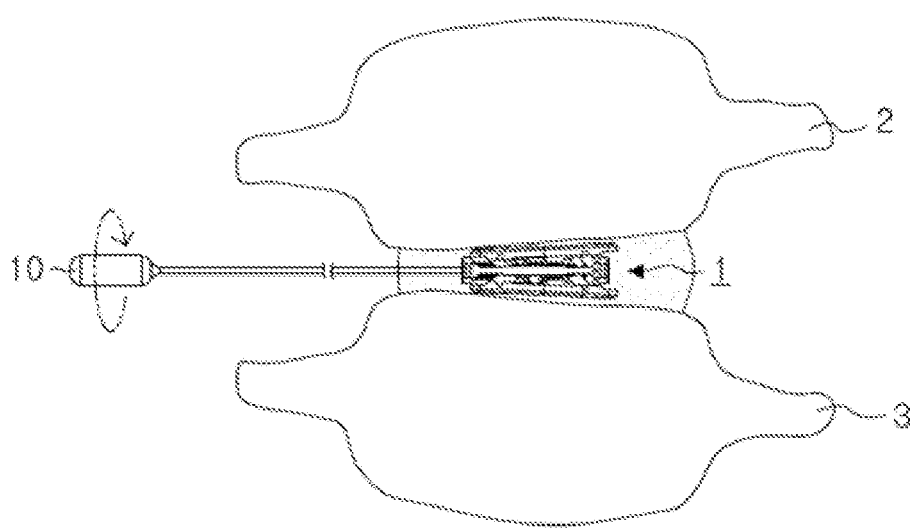
Figure 5:
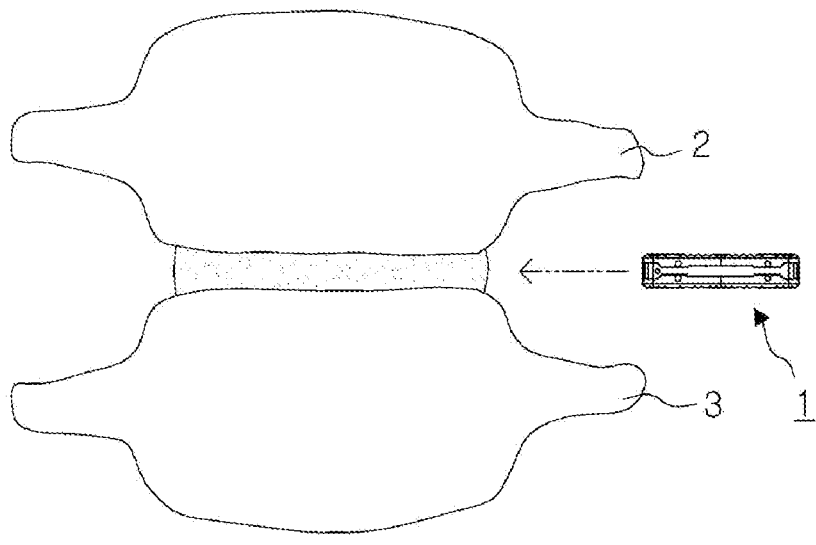
FIG. 5 is an illustrative view of the expandable cage inserted from the left side of the spine.
Figure 6:
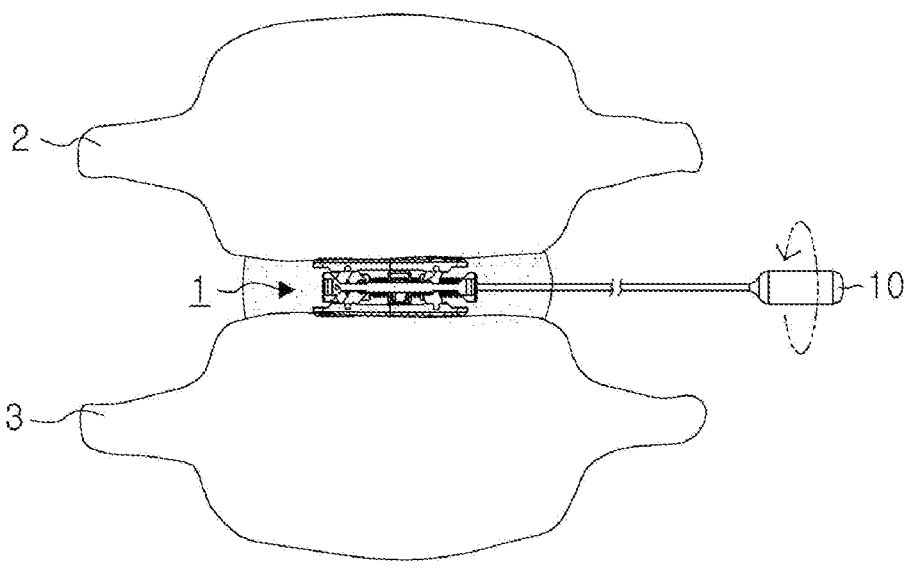
FIG. 6 is an operational illustration showing the adjustment of the spine's sagittal balance after the insertion of the expandable cage for the spine.
Figure 7A:
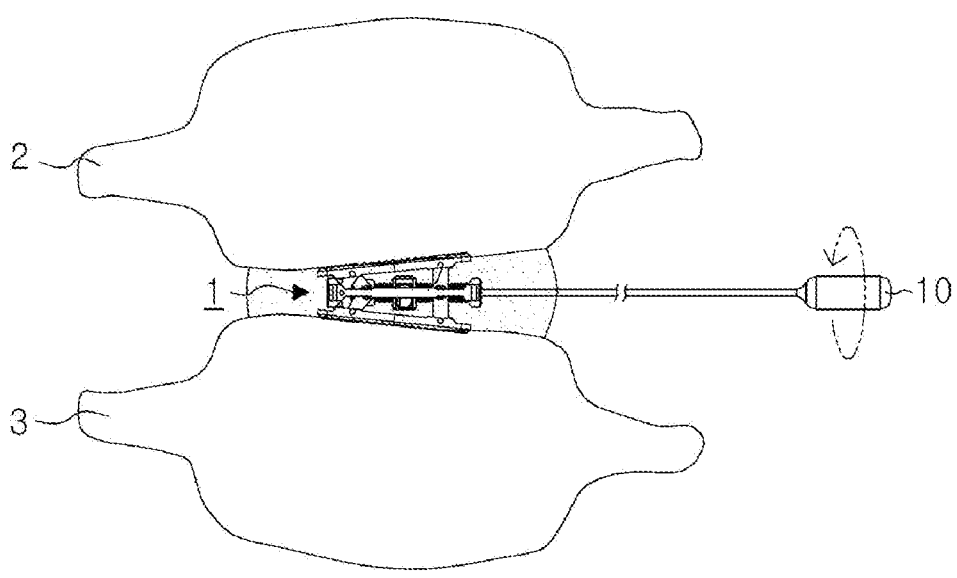
FIGS. 7A and 7B are operational views illustrating the adjustment of the coronal balance of the spine after the insertion of the expandable cage for the spine.
Figure 7B:
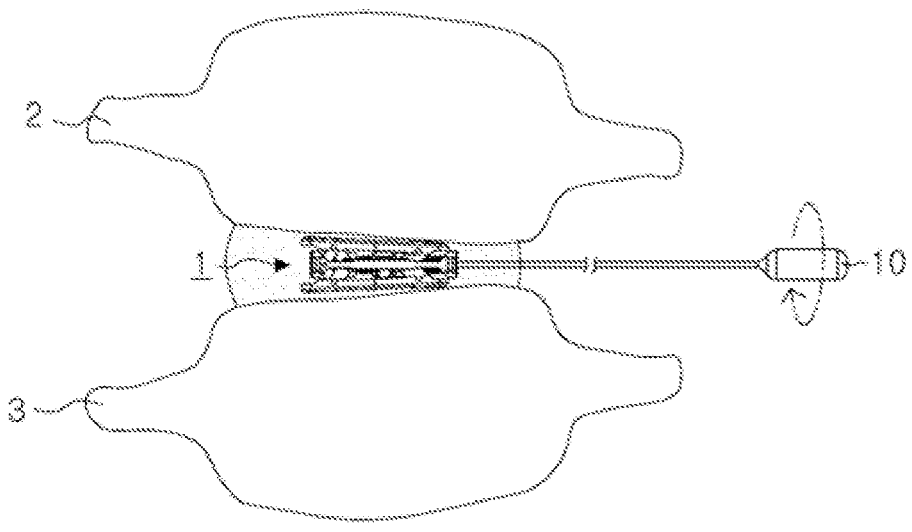
Figure 8:
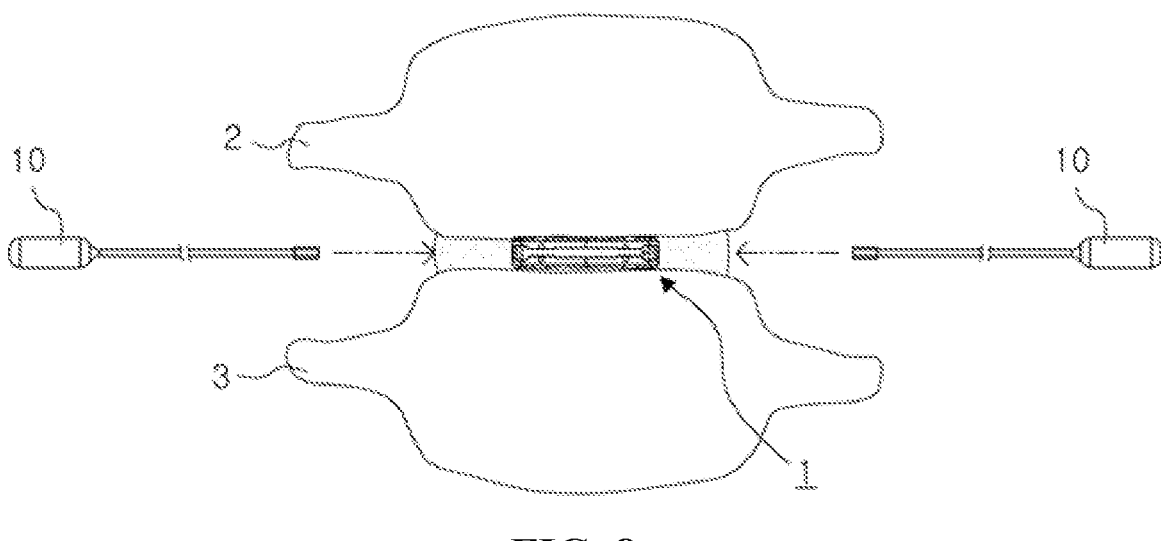
FIG. 8 is an illustrative view showing a control mechanism being insertable from the left and right lateral sides of the spine after the insertion of the expandable cage into the spine.
Figure 9:
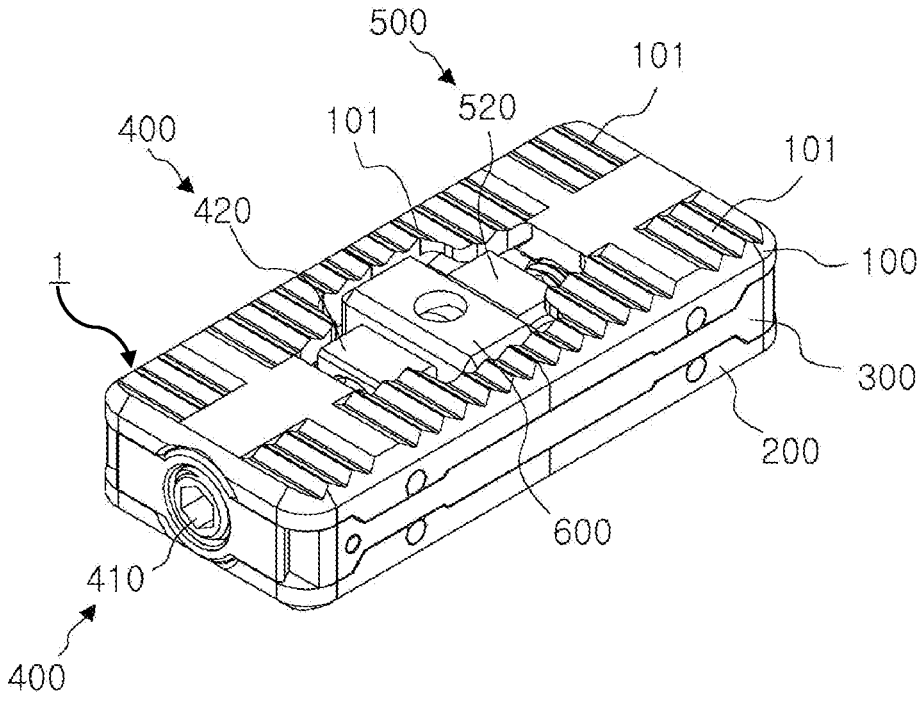
FIG. 9 is a perspective view of an expandable cage for a spine according to an embodiment of the present invention.

FIG. 1A is a view illustrating an expandable cage for a spine according to an embodiment of the present invention inserted into the spine, viewed from the sagittal plane of the spine, FIG. 1B is a view illustrating the expandable cage of FIG. 1A inserted into the spine in a different direction, viewed from the sagittal plane of the spine, FIG. 2 is an illustrative view of the expandable cage inserted from the right side of the spine, FIG. 3 is an operational view illustrating the adjustment of the sagittal balance of the spine after the insertion of the expandable cage for the spine, FIGS. 4A and 4B are operational view illustrating the adjustment of the coronal balance of the spine after the insertion of the expandable cage for the spine, FIG. 5 is an illustrative view of the expandable cage inserted from the left side of the spine, FIG. 6 is an operational illustration showing the adjustment of the spine's sagittal balance after the insertion of the expandable cage for the spine, FIGS. 7A and 7B are operational views illustrating the adjustment of the coronal balance of the spine after the insertion of the expandable cage for the spine, FIG. 8 is an illustrative view showing an control mechanism being insertable from the left and right lateral sides of the spine after the insertion of the expandable cage into the spine, and FIG. 9 is a perspective view of an expandable cage for a spine according to an embodiment of the present invention.

Figure 10:
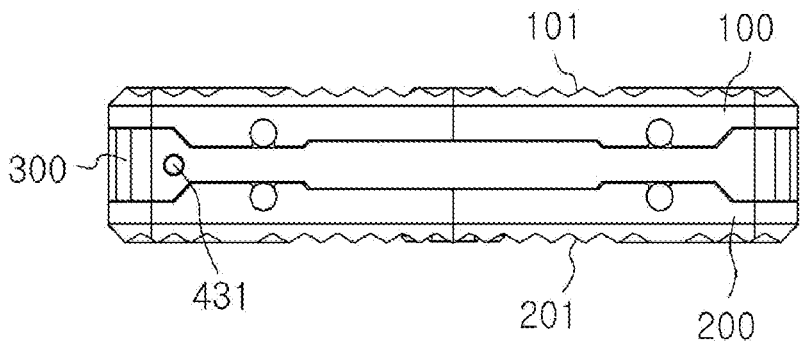
FIG. 10 is a front view of FIG. 9.
Figure 11A:
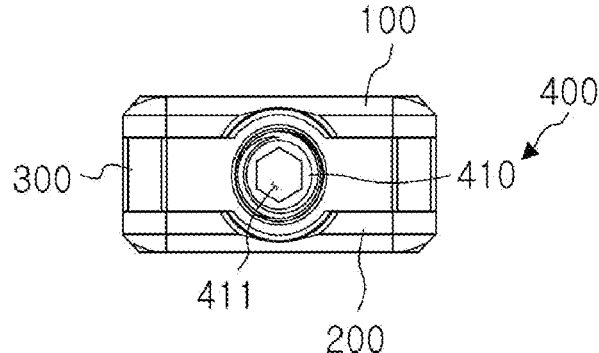
FIG. 11A is a left side view of FIG. 9.
Figure 11B:
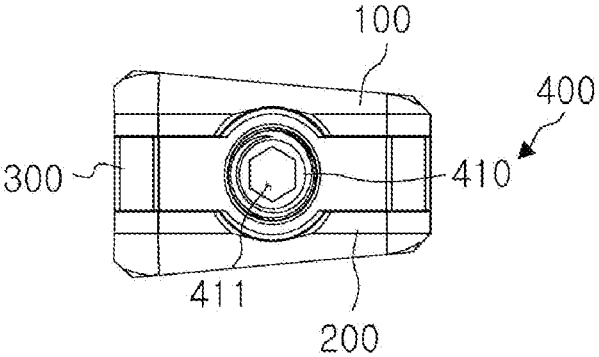
FIG. 11B is an illustrative view showing a state in which the expandable cage for the spine forms an inclination.
Figure 12A:
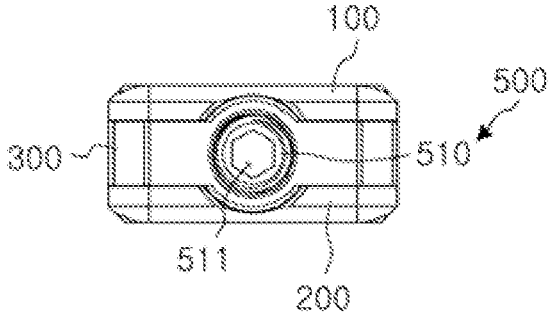
FIG. 12A is a right side view of FIG. 9.
Figure 12B:
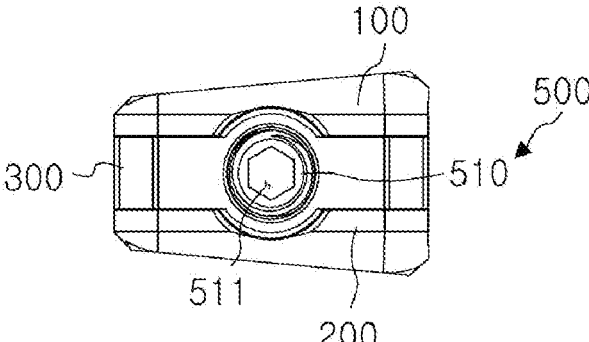
FIG. 12B is an illustrative view showing a state in which the expandable cage for the spine forms an inclination.
Figure 13:
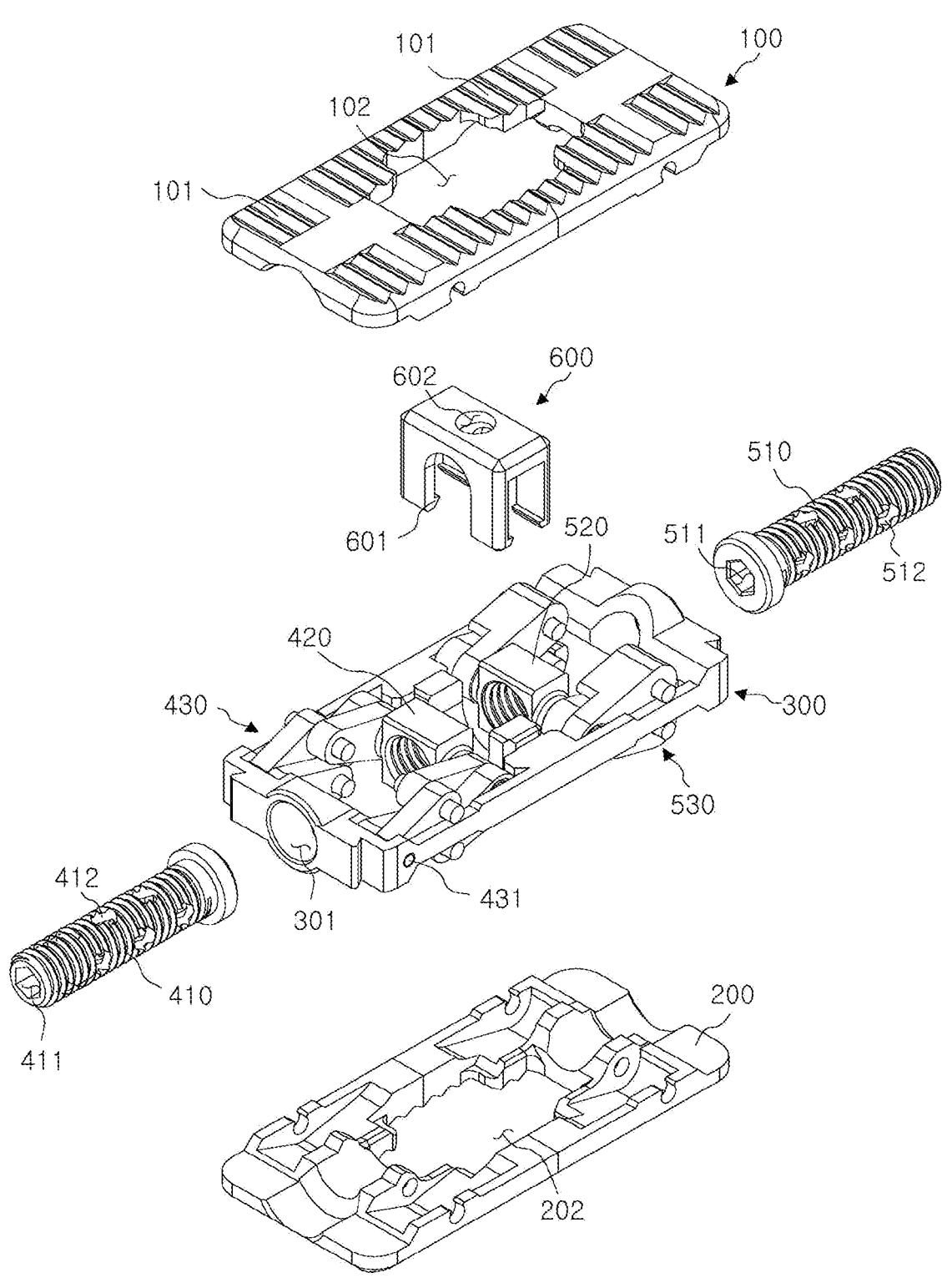
FIG. 13 is an exploded view of the expandable cage for the spine according to an embodiment of the present invention.

Moreover, FIG. 10 is a front view of FIG. 9, FIG. 11A is a left side view of FIG. 9, and FIG. 11B is an illustrative view showing a state in which the expandable cage for the spine forms an inclination, FIG. 12A is a right side view of FIG. 9, and FIG. 12B is an illustrative view showing a state in which the expandable cage for the spine forms an inclination, and FIG. 13 is an exploded view of the expandable cage for the spine according to an embodiment of the present invention.

Figure 14:
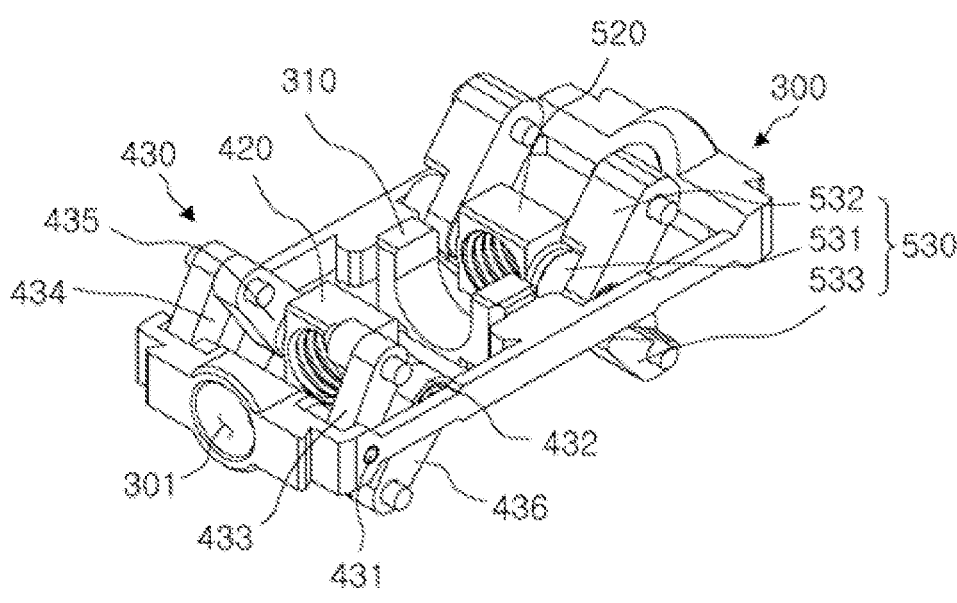
FIG. 14 is a part diagram showing the detailed configuration of a main frame.
Figure 15:
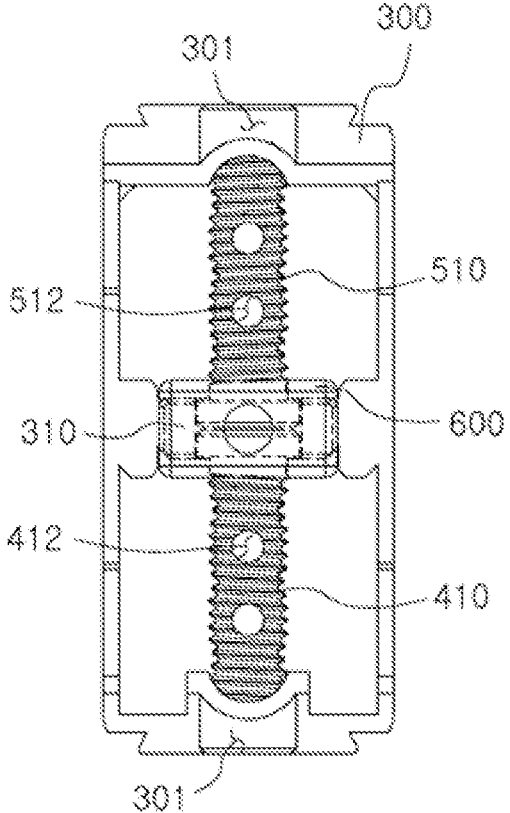
FIG. 15 is a plan projection showing a state in which a height adjusting screw and an inclination adjusting screw are accommodated in a guide.
Figure 16:
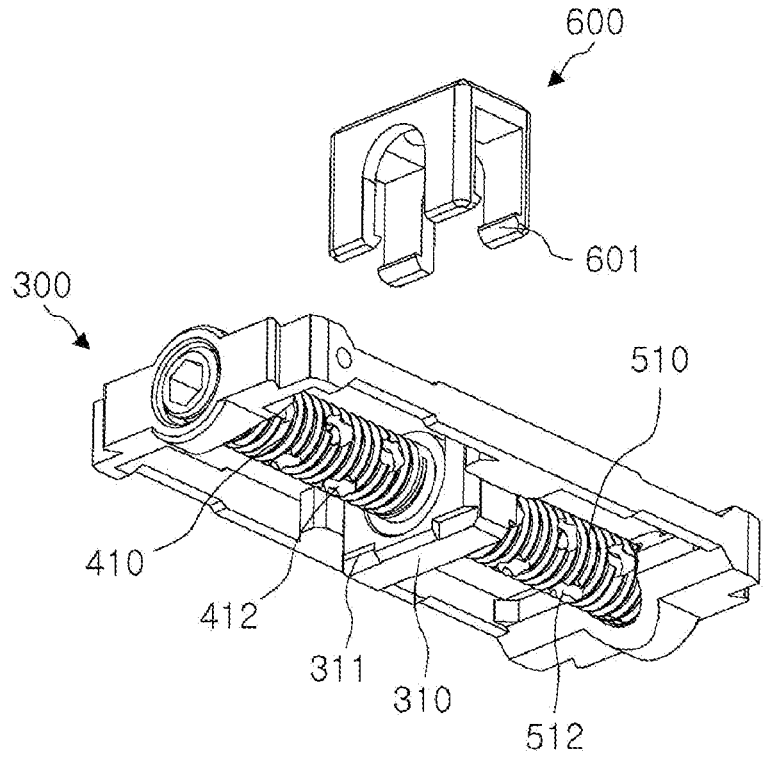
FIG. 16 is a bottom perspective view showing the detailed configuration of FIG. 15.

Additionally, FIG. 14 is a part diagram showing the detailed configuration of a main frame, FIG. 15 is a plan projection showing a state in which a height adjusting screw and an inclination adjusting screw are accommodated in a guide, and FIG. 16 is a bottom perspective view showing the detailed configuration of FIG. 15.

Figure 17:
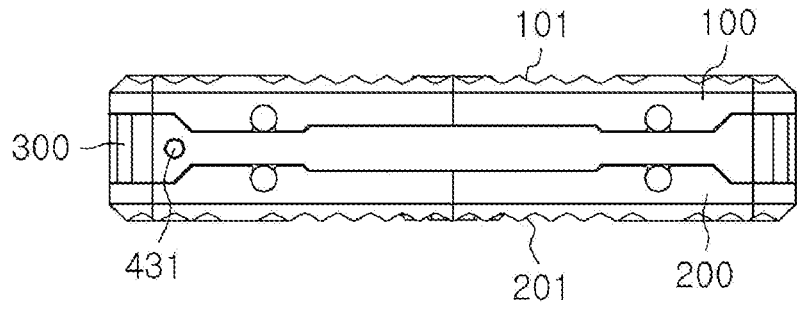
FIG. 17 is an operational view of the expandable cage for the spine according to an embodiment of the present invention.
Figure 17:
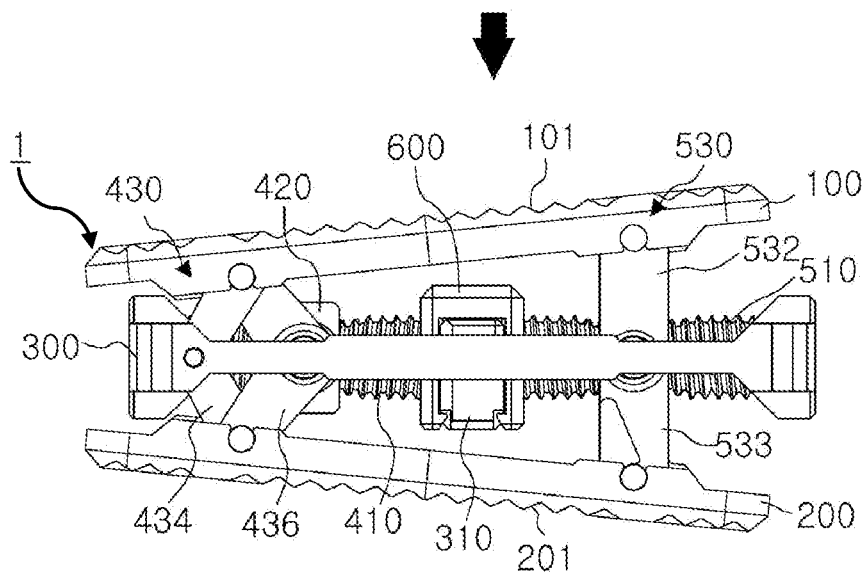
Figure 18:
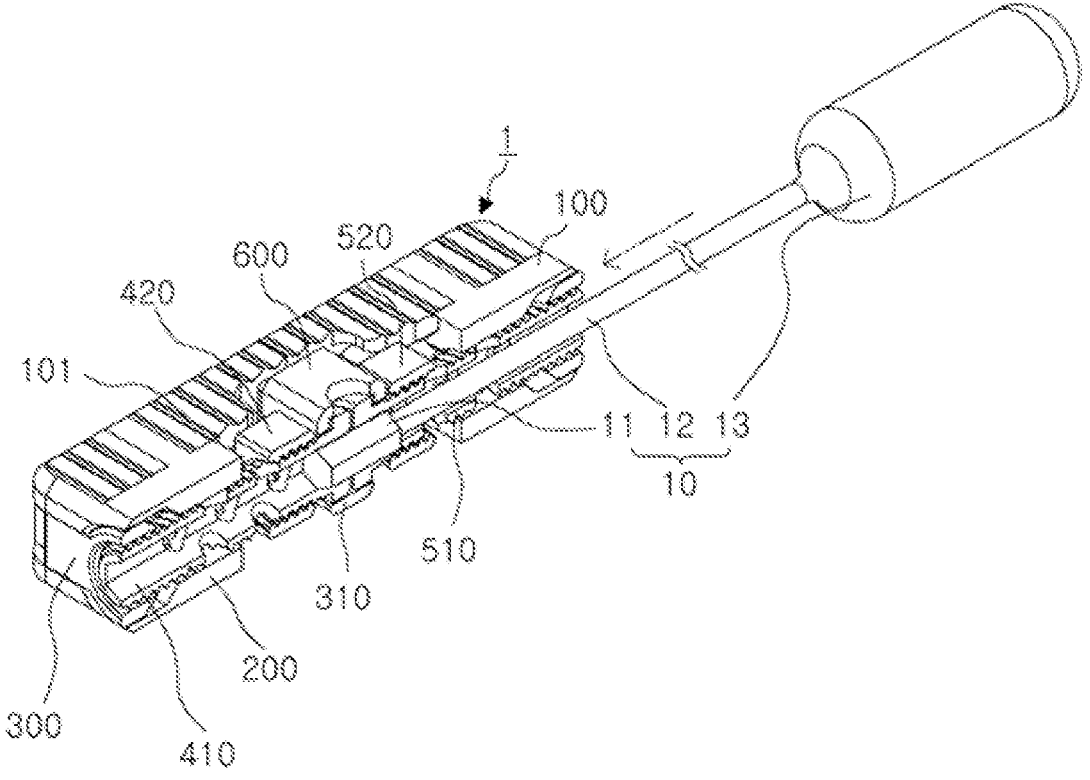
FIGS. 18 to 20B are illustrative diagrams showing the operation of the control mechanism to adjust the expandable cage for the spine from the left side of the spine.

In addition, FIG. 17 is an operational view of the expandable cage for the spine according to an embodiment of the present invention, FIGS. 18 to 20B are illustrative diagrams showing the operation of the control mechanism to adjust the expandable cage for the spine from the left side of the spine, and FIGS. 21 to 23B are illustrative diagrams showing the operation of the control mechanism to adjust the expandable cage for the spine from the right side of the spine.

Referring to FIGS. 1A and 1B, after a damaged disc is removed, the expandable cage 1 for the spine according to an embodiment of the present invention is inserted into a transplantation space between the upper vertebra 2 and the lower vertebra 3 to secure the intervertebral space. First of all, the expandable cage 1 for the spine according to an embodiment of the present invention is configured to simultaneously adjust the sagittal balance and the coronal balance of the spine, thus enabling effective treatment for complex spinal deformities.

Hereinafter, referring to the drawings, the expandable cage 1 for the spine according to an embodiment of the present invention will be described in detail.

FIG. 1A illustrates the state in which the expandable cage 1 for the spine according to an embodiment of the present invention is inserted, viewed from the sagittal plane of the spine. Referring to FIG. 1A, the expandable cage 1 for the spine can be configured to expand in a direction perpendicular to the sagittal plane of the spine (vertical direction), thereby adjusting the sagittal balance of the spine.

Moreover, as illustrated in FIG. 1B, the expandable cage can be inserted into the anterior (ALIF) or the posterior (TLIF or PLIF) of the spine, and is configured to expand in a direction perpendicular to the sagittal plane, thereby adjusting the sagittal balance of the spine.

Hereinafter, the operation method of the present invention will be described in detail.

First, FIG. 2 is a view showing an insertion method of the expandable cage 1 for the spine relative to the coronal plane of the spine. As illustrated in the drawing, the expandable cage can be inserted into the right side of the target spine. The expandable cage 1 for the spine according to an embodiment of the present invention can be configured to expand not only in a direction perpendicular to the sagittal plane of the spine but also, as illustrated, in a direction perpendicular to one side (left side in the drawing) relative to the coronal plane, thereby adjusting the coronal balance of the spine.

Specifically, referring to FIGS. 2 through 4, first, the expandable cage 1 for the spine is inserted into the transplantation space between the upper vertebra 2 and the lower vertebra 3 (FIG. 2), and the control mechanism 10 is inserted into the right side of the spine and then is rotated to operate the expandable cage 1, thereby adjusting the sagittal balance of a patient (the state where the upper vertebra 2 and the lower vertebra 3 are separated from each other, FIG. 3) and the coronal balance (the state where either to the left or right side of the spine (in this instance, the expandable cage 1 is in a state rotated 180° along the Y-axis from FIG. 2) is expanded according to a desired correction position, FIGS. 4A and 4B).

Additionally, referring to FIG. 5, the expandable cage 1 for the spine according to an embodiment of the present invention is inserted into the left side of the target spine as illustrated in the drawing, and then, can be manipulated, thereby adjusting the sagittal balance of a patient (the state where the upper spinal bone 2 and the lower vertebra 3 are separated from each other, FIG. 6) and the coronal balance (the state where either to the left or right side of the spine (in this instance, the expandable cage 1 is in a state rotated 180° along the Y-axis from FIG. 5) is expanded according to a desired correction position, FIGS. 7A and 7B).

In other words, the expandable cage 1 for the spine according to the present embodiment can be configured to expand not only in the direction perpendicular to the sagittal plane of the spine but also, as illustrated, in the direction perpendicular to one side (right side in the drawing) of the coronal plane, thereby adjusting the coronal balance of the spine.

Moreover, the insertion direction of the control mechanism 10 for adjusting the sagittal balance and the coronal balance using the expandable cage 1 can be freely chosen and changed from either the left or right side of the spine, as illustrated in FIG. 8, depending on the surgeon's surgical procedures, anatomical limitations, and the desired position for deformity correction. Through the form and configuration of the expandable cage 1, the control mechanism 10 can adjust a sagittal balance control unit 400 or a coronal balance control unit 500 located on the opposite side of the control mechanism 10, according to the insertion depth of the control mechanism, thereby reducing the burden on the patient.

In summary, the expandable cage 1 for the spine according to an embodiment of the present invention is inserted not only in a predetermined direction but also into the left side or the right side of the spine depending on the surgeon's surgical procedures, anatomical limitations, and the desired position for deformity correction, that is, the expansion operation of the cage for sagittal extension and coronal correction can be operated to approach both sides simultaneously, according to the user's choice.

Hereinafter, with reference to FIGS. 9 through 23B, the expandable cage 1 for the spine according to an embodiment of the present invention, designed to adjust the sagittal balance and the coronal balance will be described in detail.

Referring to FIGS. 9 through 23B, the expandable cage 1 for the spine according to an embodiment of the present invention can include an upper structural body 100, a lower structural body 200, a main frame 300, a sagittal balance control unit 400, and a coronal balance control unit 500.

The expandable cage 1 for the spine according to an embodiment of the present invention can be made of any one selected from metallic materials, such as titanium, carbon alloy, ceramic material, and plastic (polyether ether ketone (PEEK)), which is harmless to the human body and capable of enduring long-term impacts and loads applied to the spine. The components of the cage may be made of the same material or different materials according to the function of each component. Of course, various materials can be applied to the cage as long as they fulfill the aforementioned objectives. Hereinafter, the description will continue.

Firstly, the upper structural body 100 can be formed with predetermined area and thickness.

Specifically, the upper structural body 100 can be formed in a rectangular plane shape, considering the transplantation space, and the form and size of the disc, and can be shaped as a plate with a predetermined thickness (height).

Most preferably, the upper structural body 100 can be formed within the dimensions of a width of 18 mm to 22 mm, a length of 40 mm to 60 mm, and a height of 8 mm to 14 mm. However, the dimensions are preferred sizes considering the average transplantation space for an adult and are not limited to the specific measurements.

Furthermore, the upper structural body 100 can be fixedly coupled to the upper vertebra 2. For this purpose, the upper structural body 100 can have a flat upper surface or a first fixing force forming part 101 where the surface facing the upper vertebra 2 is formed to protrude or to be recessed with a predetermined pattern to make fixation force between directly contacting parts.

Specifically, the first fixing force forming part 101 can be formed as wedge-shaped fixation protrusions (spikes) protruding from the upper surface of the upper structural body 100 or as a porous surface to facilitate the bone growth.

Additionally, though not shown, the upper structural body 100 can be fixed to the upper vertebra 2 through a separate fixing means. Here, the fixing means can be fixing pins intended for fixation to the upper vertebra 2.

In addition, the fixing means can be integrated into the upper structural body 100 and manufactured as a single product during the manufacturing of the upper structural body 100, or can be variously configured as long as the upper structural body 100 and the upper vertebra 2 can be fixed to each other.

Moreover, the lower structural body 200 can be formed with a predetermined area and located at a predetermined distance below from the upper structural body 100.

More specifically, the lower structural body 200 can be formed in a rectangular plane shape corresponding to the plane shape of the upper structural body 100, and shaped as a plate with a predetermined thickness (height).

Furthermore, the lower structural body 200 can be formed in dimensions corresponding to the above-described upper structural body 100 within the dimensions of a width of 18 mm to 22 mm, a length of 40 mm to 60 mm, and a height of 8 mm to 14 mm, however, the present invention is not limited to the dimensions.

Additionally, the surface of the lower structural body 200 can also have a second fixing force forming part 201 where the surface facing the lower vertebra 3 is formed to protrude or to be recessed with a predetermined pattern to make fixation force between directly contacting parts.

Specifically, the second fixing force forming part 201 can be formed as wedge-shaped fixation protrusions (spikes)

protruding from the upper surface of the lower structural body 200 or as a porous surface to facilitate the bone growth.

The lower structural body 200 can be positioned spaced apart from the upper structural body 100 and have a flat bottom surface. The same fixing means described earlier for the upper structural body 100 can be similarly applied to the lower structural body 200, and the lower portion of the lower structural body 200 can be fixed to the lower vertebra 3.

Referring to the above, when viewing a normal human spine from the side (sagittal plane), in order to disperse the gravity force vertically applied to the spine the most efficiently, the cervical spine curves forward (cervical lordosis), the thoracic spine curves backward (thoracic kyphosis), and the lumbar spine curves forward again (lumbar lordosis), so as to form a typical S-shaped curvature.

Meanwhile, the human spine is comprised of 26 bones, including 5 lumbar vertebrae, with 5 discs between the vertebra to absorb shock.

In this instance, the discs are respectively compressed in a way that causes the lumbar spine to curve forward, especially in the lumbar region where the center of gravity is more posterior and greater loads are applied to the back. So, the discs are pressed into a wedge shape, so the discs also have the corresponding wedge shape.

Therefore, preferably, the expandable cage 1 for the spine according to the present invention is formed in a wedge shape on the sagittal plane to correspond with the disc shape.

Meanwhile, as illustrated in FIGS. 11A and 12A, the upper structural body 100 and the lower structural body 200 can be formed to be parallel to each other, i.e., to have an inclination angle of 0°. However, as illustrated in FIGS. 11B and 12B, the upper surface of the upper structural body 100 can be inclined downward from one side of the spine to the other relative to the sagittal plane of the spine, and the bottom surface of the lower structural body 200 can be inclined upward in the same manner.

In this instance, the upper surface of the upper structural body 100 and the bottom surface of the lower structural body 200 having the inclinations can be formed symmetrically to the horizontal plane, and the upper structural body and the lower structural body have the same the inclination angle within the range of 8° to 10° relative to the horizontal plane.

Considering that, when viewed from the side, the curvature angles of the cervical and thoracic spines of normal persons are between 20° to 40° and the lumbar spine (including the first sacral vertebra) is between 30° to 50°, given that the lumbar spine consists of five discs and the cumulative wedge angle of the five discs forms the total curvature of 30° to 50°, the angle of each disc can be approximately 8° to 10°.

In other words, all five lumbar discs do not have the same angle, but the individual angles are almost similar, excluding the lowest disc. Accordingly, assuming the five discs collectively form a lumbar angle ranging from 30° to 50°, the angle of each disc could be within the range of 8° to 10°, but the angles are not strictly limited thereto.

Accordingly, the expandable cage 1 for the spine according to the present invention, as illustrated in FIGS. 10 to 12, can have an overall shape that is either rectangular or trapezoidal, and have one side and the other side which are symmetrical to each other relative to the insertion direction. Accordingly, during insertion, the anterior and posterior direction can be changed to vary the expansion position for adjusting the coronal balance.

That is, the expandable cage 1 according to an embodiment of the present invention can allow expansion on both the left and right sides of the spine by simply changing the direction, thus minimizing incision sites.

Meanwhile, in case of the upper structural body 100 and the lower structural body 200 which form the exterior of the expandable cage 1 according to an embodiment of the present invention, the upper structural body 100 can have an upper through-hole 102 of a long hole type formed to facilitate effective bone fusion with the upper vertebra 2 and the lower vertebra 3 after the insertion between the vertebrae, and the lower structural body 200 can have a lower through-hole 202.

Here, the sizes, shapes, and positions of the upper through-hole 102 and the lower through-hole 202 can be designed in various ways.

Moreover, the main frame 300 is positioned between the upper structural body 100 and the lower structural body 200, and can have control mechanism insertion holes 301 on both sides in the longitudinal direction for the insertion of the control mechanism 10.

In this instance, as illustrated in FIG. 13, the control mechanism insertion holes 301 can be formed without a screw thread to merely guide the insertion of the control mechanism 10, or can have a screw thread to guide the rotational movement of the control mechanism 10.

Moreover, the main frame 300 can be formed within the dimensions of a width of 18 mm to 22 mm and a length of 40 mm to 60 mm to correspond to the upper structural body 100 and the lower structural body 200, but is not limited thereto.

Additionally, the main frame 300 can have a seating member 310 provided at the longitudinal midpoint thereof, so that end portions of the height adjusting screw 410 and the inclination adjusting screw 510, which will be described in detail later, can be placed thereon.

In addition, the sagittal balance control unit 400 can be coupled to the main frame 300 and attached to one side of each of the upper structural body 100 and the lower structural body 200 to the distance between the upper structural body 100 and the lower structural body 200 by the control mechanism 10 inserted into the control mechanism insertion hole 301, thereby adjusting the sagittal balance of the spine.

More specifically, the sagittal balance control unit 400 serves to adjust the sagittal balance of the spine. In this instance, the sagittal balance refers to adjusting the curvature of the spine on the sagittal plane (when viewed from the side) to achieve an ideal curved form. The sagittal balance control unit 400 is positioned between the upper structural body 100 and the lower structural body 200 and is configured to adjust the distance, namely, the height, between the upper structural body 100 and the lower structural body 200. In detail, by increasing the distance between the upper structural body 100 and the lower structural body 200 so that they remain parallel, thereby adjusting the sagittal balance of the spine.

For this purpose, the sagittal balance control unit 400 may include a height adjusting screw 410, a height adjusting member 420, and a height adjusting link 430.

Firstly, the height adjusting screw 410 is positioned between the upper structural body 100 and lower structural body 200 and arranged in longitudinal direction of the upper structural body 100 and lower structural body 200. The height adjusting screw 410 has a screw thread formed on the outer circumferential surface thereof, and the control mechanism 10 is inserted into the height adjusting screw 410 so that the height adjusting screw 410 rotates in conjunction with the rotation of the control mechanism 10.

Moreover, the height adjusting screw 410 has a cylindrical shape and a screw thread formed on the outer circumferential surface thereof, and includes a first adjusting hole 411 through which the control mechanism 10 can be inserted.

Furthermore, the height adjusting screw 410 can rotate in response to the rotation of the control mechanism 10 inserted therein, and has a polygonal cross-sectional shape of the first adjusting hole 411 formed to facilitate the rotation. As illustrated in the drawings, the first adjusting hole 411 has a hexagonal cross-sectional shape, and the control mechanism 10 can be applied to correspond to the cross-sectional shape of the first adjusting hole 411.

Here, the control mechanism 10 is formed to a predetermined length, and includes: a hexagonal head part 11 having a hexagonal cross-sectional shape corresponding to the cross-sectional shape of the first adjusting hole 411; a cylindrical rod part 12 which is connected to the hexagonal head part 11, has a circular cross-section, and is smaller in diameter than the hexagonal head part 11; and a handle part 13 which allows a user to grasp it.

At this time, the hexagonal head part 11 is preferably formed to a length ranging from 8 mm to 12 mm, considering the insertion depth into the first adjusting hole 411, but is not limited thereto. The length of the hexagonal head part 11 can be vary considering that it is simultaneously inserted into the second adjusting hole 511 of the inclination adjusting screw 510 and the first adjusting hole 411 to concurrently rotate the height adjusting screw 410 and the inclination adjusting screw 510.

Furthermore, the height adjusting screw 410, depending on the rotation, moves the height adjusting member 420 to determine a movement distance of the height adjusting member 420 according to the pitch of the screw thread, and the movement distance determines the distance between the upper structural body 100 and the lower structural body 200.

Therefore, the height adjusting screw 410 can set the pitch of the screw thread according to a distance adjustment range between the upper structural body 100 and the lower structural body 200.

Additionally, the height adjusting screw 410 supports and maintains the distance between the upper structural body 100 and the lower structural body 200 due to the screw-coupling force with the height adjusting member 420. Considering the screw-coupling force, the pitch and form of the screw thread can be varied.

In addition, the height adjusting member 420 has a screw hole that is concentric with the control mechanism insertion hole 301, and can be screw-coupled to the height adjusting screw 410 to move due to the rotation of the height adjusting screw 410.

More specifically, the height adjusting member 420 is screw-coupled to the height adjusting screw 410 to reciprocally move along the height adjusting screw 410. Due to the movement, the distance between the upper structural body 100 and the lower structural body 200 increases, thereby vertically expanding the expandable cage 1 for the spine on the sagittal plane.

Furthermore, the height adjusting link 430 has an upper end which is connected to the upper structural body 100 and lower end which is connected to the lower structural body 200, and is linked to the height adjusting member 420, thereby allowing for the adjustment of the height between the upper structural body 100 and the lower structural body 200 due to the movement of the height adjusting member 420.

Here, the height adjusting link 430 can include a fixed shaft 431, a moving shaft 432, a first height adjusting link frame 433, a second height adjusting link frame 434, a third height adjusting link frame 435, and a fourth height adjusting link frame 436.

Firstly, the fixed shaft 431 can be fixed and joined to the main frame 300.

Additionally, the moving shaft 432 can be provided on the height adjusting member 420.

In addition, the first height adjusting link frame 433 is formed to have a certain length, and has one side rotatably coupled to the fixed shaft 431 and the other side rotatably coupled to the upper structural body 100.

Moreover, the second height adjusting link frame 434 can have one side rotatably coupled to the fixed shaft 431 and the other side rotatably connected to the lower structural body 200.

Furthermore, the third height adjusting link frame 435 can have one side rotatably coupled to the moving shaft 432 and the other side rotatably coupled to the upper structural body 100.

Additionally, the fourth height adjusting link frame 436 can also have one side rotatably coupled to the moving shaft 432 and the other side rotatably coupled to the lower structural body 200.

Accordingly, the height adjusting link 430 can have a rhomboidal link structure, whereby the height between the upper structural body 100 and the lower structural body 200 is adjusted due to the distance between the moving shaft 432 and the fixed shaft 431.

In addition, the coronal balance control unit 500 is coupled to the main frame 300 and coupled to the other side of each of the upper structural body 100 and the lower structural body 200, so as to adjust the inclination of the upper structural body 100 and the lower structural body 200 by lifting and lowering each of the upper structural body 100 and the lower structural body 200 by the control mechanism 10, thereby adjusting the coronal balance of the spine.

Specifically, the coronal balance control unit 500 serves to adjust the coronal balance of the spine and to control the imbalance on the coronal plane (viewed from the front) of the spine so that the spine achieves an ideal coronal plane balance. The coronal balance control unit 500 is positioned between the upper structural body 100 and the lower structural body 200 and is coupled to one side of each of the upper structural body 100 and the lower structural body 200, so as to adjust the transverse (longitudinal) inclination of the upper structural body 100 and the lower structural body 200 by lifting and lowering each of the upper structural body 100 and the lower structural body 200, thereby adjusting the coronal balance of the spine.

The coronal balance control unit 500 may include an inclination adjusting screw 510, an inclination adjusting member 520, and an inclination adjusting link 530.

Firstly, the inclination adjusting screw 510 is arranged in the longitudinal direction between the upper structural body 100 and the lower structural body 200, has a screw thread formed on the outer circumferential surface thereof. The control mechanism 10 is inserted into the inclination adjusting screw 510 such that the inclination adjusting screw 510 can rotate in response to the rotation of the control mechanism 10.

More specifically, the inclination adjusting screw 510 is positioned in the transverse direction between the upper structural body 100 and the lower structural body 200, has a screw thread formed in a cylindrical shape the outer circumferential surface thereof, and includes a second adjusting hole 511 formed for the insertion of the control mechanism 10, which rotates in response to the rotation of the control mechanism 10.

Additionally, the second adjusting hole 511 of the inclination adjusting screw 510 is formed to have the same diameter and cross section as the first adjusting hole 411. The inclination adjusting screw 510 is aligned with the height adjusting screw 410, such that the first adjusting hole 411 and the second adjusting hole 511 are coaxially arranged.

Accordingly, depending on the surgeon's surgical procedures, anatomical limitations, and the desired position for deformity correction, the control mechanism 10 can approach an appropriate position (left or right of the patient), namely, the inclination adjusting screw 510 can be rotated by the same control mechanism 10, which rotates the height adjusting screw 410. So, during the adjustment of the sagittal balance and the coronal balance, depending on the insertion depth of the control mechanism 10, both of the inclination adjusting screw 510 and the height adjusting screw 410 can be rotated or any one of the inclination adjusting screw 510 and the height adjusting screw 410 can be rotated selectively, thereby facilitating the adjustment of the sagittal balance and the coronal balance.

Meanwhile, when the inclination adjusting screw 510 and the height adjusting screw 410 are rotated by the rotation of the control mechanism 10, the screw threads formed on the outer circumferential surfaces of the inclination adjusting screw 510 and the height adjusting screw 410 are formed in the opposite direction to each other.

Accordingly, the height adjusting member 420 and the inclination adjusting member 520 move symmetrically in response to the unidirectional rotation of the control mechanism 10.

That is, since the screw threads of the inclination adjusting screw 510 and the height adjusting screw 410 are formed in the opposite direction to each other, the inclination adjusting screw 510 and the height adjusting screw 410 rotate in different directions from each other, and the height adjusting member 420 and the inclination adjusting member 520, which move in screw-coupling with the inclination adjusting screw 510 and the height adjusting screw 410 move symmetrically to each other inwards and outwards.

Thus, even when the control mechanism 10 simultaneously rotates both the inclination adjusting screw 510 and the height adjusting screw 410, the height adjusting member 420 and the inclination adjusting member 520 will perform the same expansion or contraction operation.

Meanwhile, the height adjusting screw 410 and the inclination adjusting screw 510 provided to adjust the height and inclination of the expandable cage 1 can respectively have screw through-holes 412 and 512, which are formed vertically for effective bone fusion between the upper vertebra 2 and the lower vertebra 3 after the insertion between the vertebrae. In this instance, the screw through-holes 412 and 512 are not necessarily perpendicular to the screw but can be provided at a diagonally intersecting position in the longitudinal direction of the height adjusting and the inclination adjusting screws, and their size and shape can be varied.

Additionally, the inclination adjusting member 520 has a screw hole concentric with the control mechanism insertion hole 301 and can be screw-coupled to the inclination adjusting screw to reciprocate in response to the rotation of the inclination adjusting screw.

Furthermore, the inclination adjusting link 530 has one side connected to the upper structural body 100 and the other side connected to the lower structural body 200, and can adjust the inclination formed by the upper and lower structural bodies based on the movement of the inclination adjusting member 520.

Here, the inclination adjusting link 530 may include a rotational shaft 531, a first inclination adjusting link frame 532, and a second inclination adjusting link frame 533.

Firstly, the rotational shaft 531 can be provided on the inclination adjusting member 520.

Moreover, the first inclination adjusting link frame 532 can have one side rotatably coupled to the rotational shaft 531 and the other side rotatably coupled to the upper structural body 100.

Furthermore, the second inclination adjusting link frame 533 can have one side rotatably coupled to the rotational shaft 531 and the other side rotatably coupled to the lower structural body 200.

Accordingly, when the inclination adjusting screw 510 rotates, the inclination adjusting member 520 that is screw-coupled to the inclination adjusting screw 510 moves inwardly along the inclination adjusting screw 510. Subsequently, as the inclination adjusting member 520 moves inwardly, the distance between the upper structural body 100 and the lower structural body 200 increases by the inclination adjusting link 530 connected to the inclination adjusting member 520, such that one side of the expandable cage 1 is expanded relative to the coronal plane.

Additionally, the expandable cage 1 for the spine according to an embodiment of the present invention further includes a guide member 600, which is provided within the main frame 300 to move freely, is formed to accommodate end portions of the height adjusting screw 410 and the inclination adjusting screw 510, which are inserted in opposite directions to each other, thereby guiding both the height adjusting screw 410 and the inclination adjusting screw 510.

More specifically, the guide member 600 may have a coupling protrusion 601 that can interlock with the seating member 310, where the bottom surfaces of the height adjusting screw 410 and the inclination adjusting screw 510 are seated. Correspondingly, the seating member 310 may have a coupling groove 311 provided on the bottom surface of the seating member 310 to accommodate the coupling protrusion 601 of the guide member 600.

Additionally, the guide member 600 can also have through-holes 602 formed in the upper surface thereof. The through-holes 602 are designed to be present in the upper structural body 100, the lower structural body 200, the height adjusting screw 410, and the inclination adjusting screw 510 to facilitate effective bone fusion between the upper vertebra 2 and the lower vertebra 3 after the insertion between the vertebrae.

Hereinafter, the operation method of the present invention will be described.

The expandable cage 1 for the spine according to the present invention can be inserted into the transplantation space between the upper vertebra 2 and the lower vertebra 3 via lateral approach (trans-psoas approach) or anterolateral approach (ante-psoas approach).

Therefore, the expandable cage 1 according to an embodiment of the present invention can bypass major blood vessels, differently from the conventional method that the cage is inserted from the rear side of the spine, and reduce the risk of muscle or ligament damage, thereby enabling safer surgical procedures. However, the insertion method of the cage is not limited to the lateral approach, and depending on the surgical method, can also be inserted anteriorly (ALIF) or posteriorly (TLIF or PLIF).

First, the method of performing coronal and sagittal adjustments using the control mechanism 10 inserted into the sagittal balance control unit 400.

Since the expandable cage 1 for the spine according to the present invention which adopts the lateral approach or the anterolateral approach, the insertion method can be performed by an insertion tool (not shown) for effective insertion.

The insertion tool can include a distractor and a slide. Here, the distractor serves to widen the transplantation space to previously expand a space where the expandable cage 1 will be inserted. The slide serves to cover and insert upper and lower portions of the expandable cage 1 into the transplantation space widened by distractor.

So, the user can insert the expandable cage 1, which is not expanded, into the transplantation space by using the insertion tool.

As described above, the spinal expandable cage 1 is designed such that the height on one side (anterior) is higher than the other (posterior) based on the sagittal plane, so the upper surface of the upper structural body 100 and the lower surface of the lower structural body 200 are inclined.

Therefore, when the expandable cage 1 is inserted into the transplantation space, the user inserts the expandable cage 1 in such a way that the higher side of the cage faces one side of the spine. After the insertion of the expandable cage 1 into the transplantation space, the user can adjust the sagittal balance and the coronal balance according to the patient's vertebral conditions. Referring to FIGS. 17 to 23B, the operation of the expandable cage 1 will be described in more detail in relation to the adjustment methods of the sagittal balance and the coronal balance.

Firstly, the sagittal balance control unit 400 can expand the distance between the upper structural body 100 and the lower structural body 200 based on the sagittal plane of the spine to adjust the sagittal balance of the spine. The user inserts the control mechanism 10 so that the hexagonal head 11 is coupled with the first adjusting hole 411 of the height adjusting screw 410 and the second adjusting hole 511 of the inclination adjusting screw 510.

Then, in the above state, when the user rotates the control mechanism 10, both the height adjusting screw 410 and the inclination adjusting screw 510 are rotated simultaneously to expand the distance between the upper and lower structural bodies, thereby adjusting the sagittal balance. In order to adjust the sagittal balance, the hexagonal head 11 of the control mechanism 10 is inserted into both the first adjusting hole 4111 and the second adjusting hole 511, but it is also possible to adjust the sagittal balance by coupling the hexagonal head 11 only with the first adjusting hole 411 and rotating the height adjusting screw 410.

Figure 19:
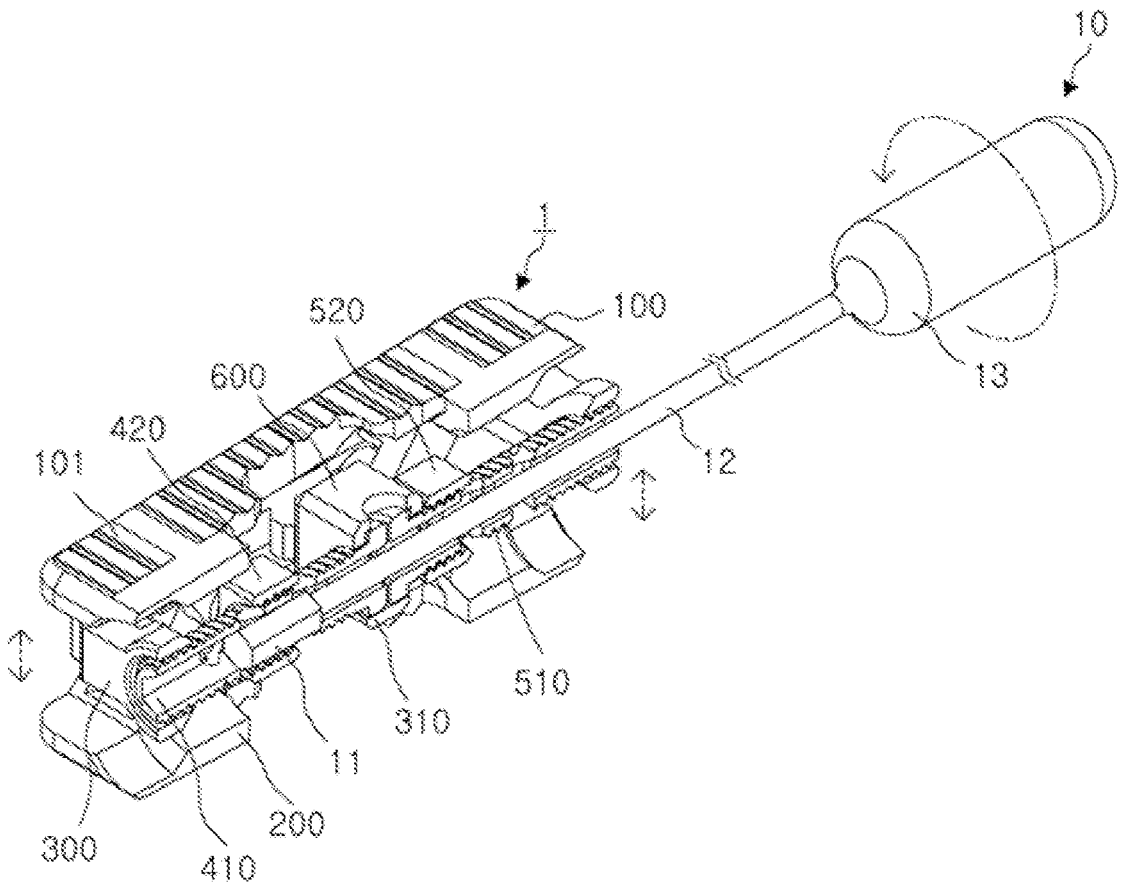
Figure 20A:
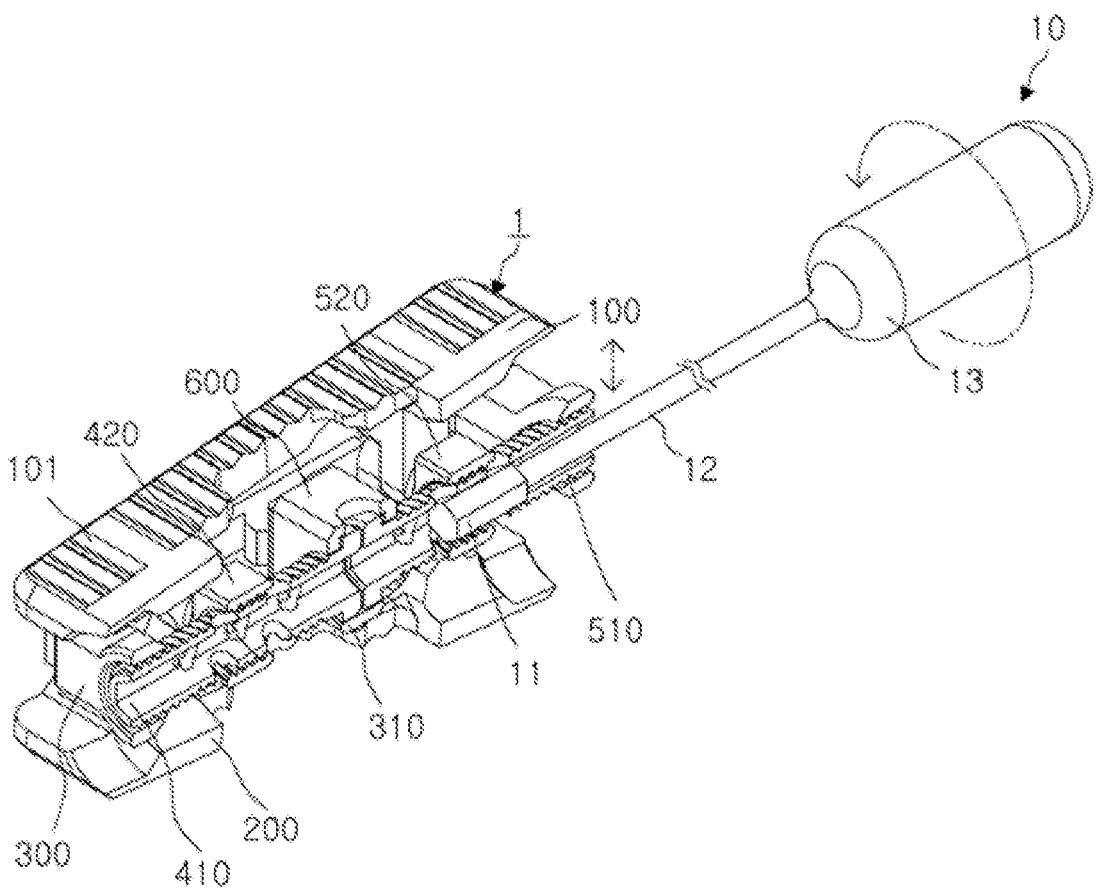
Figure 20B:
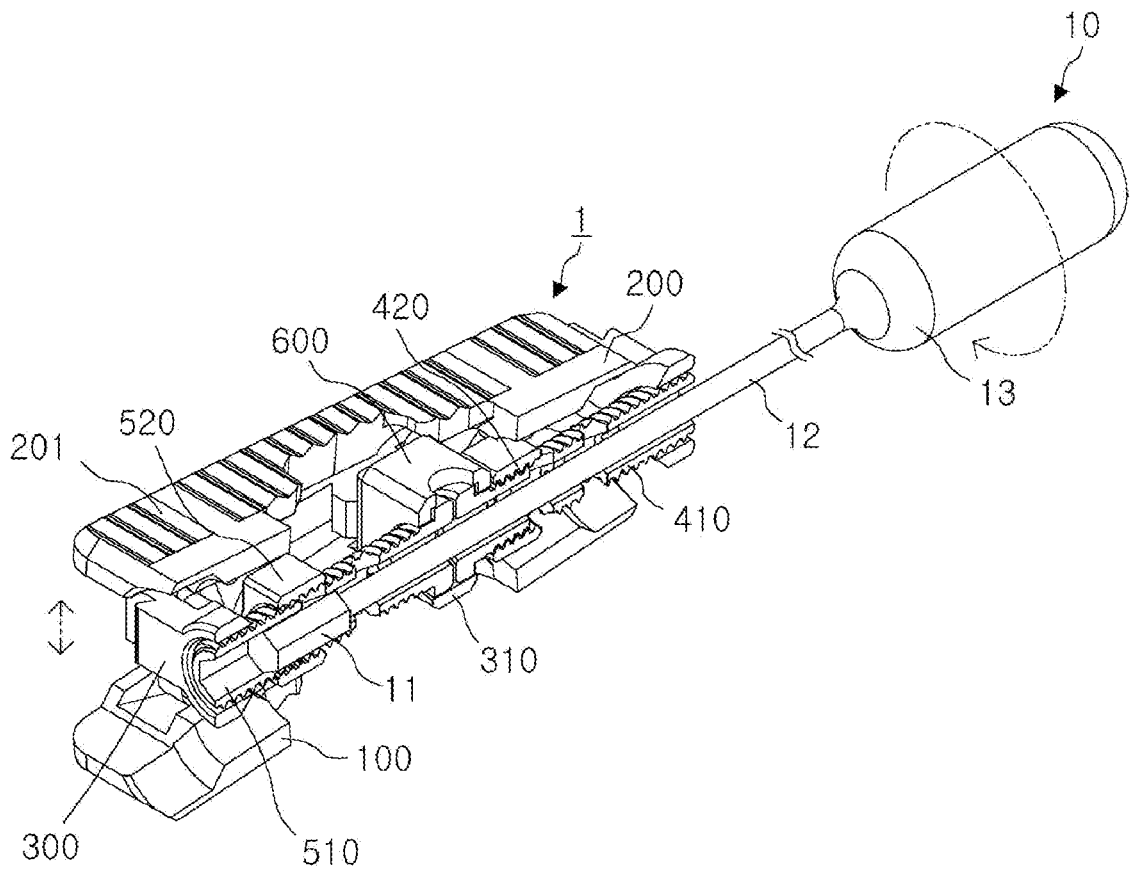
Figure 21:
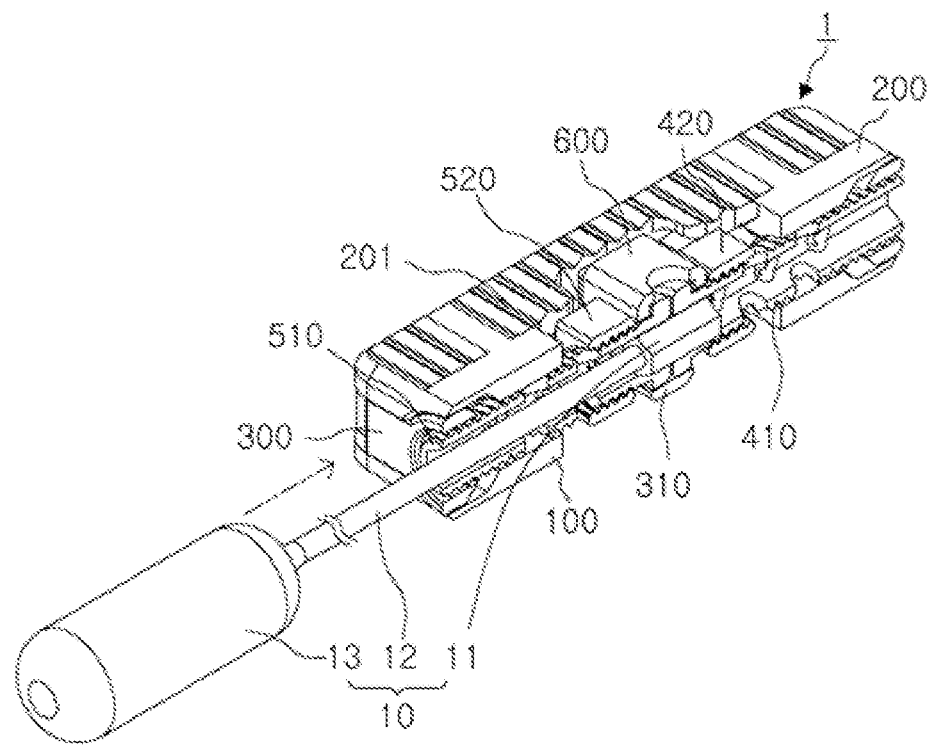
FIGS. 21 to 23B are illustrative diagrams showing the operation of the control mechanism to adjust the expandable cage for the spine from the right side of the spine.
Figure 22:
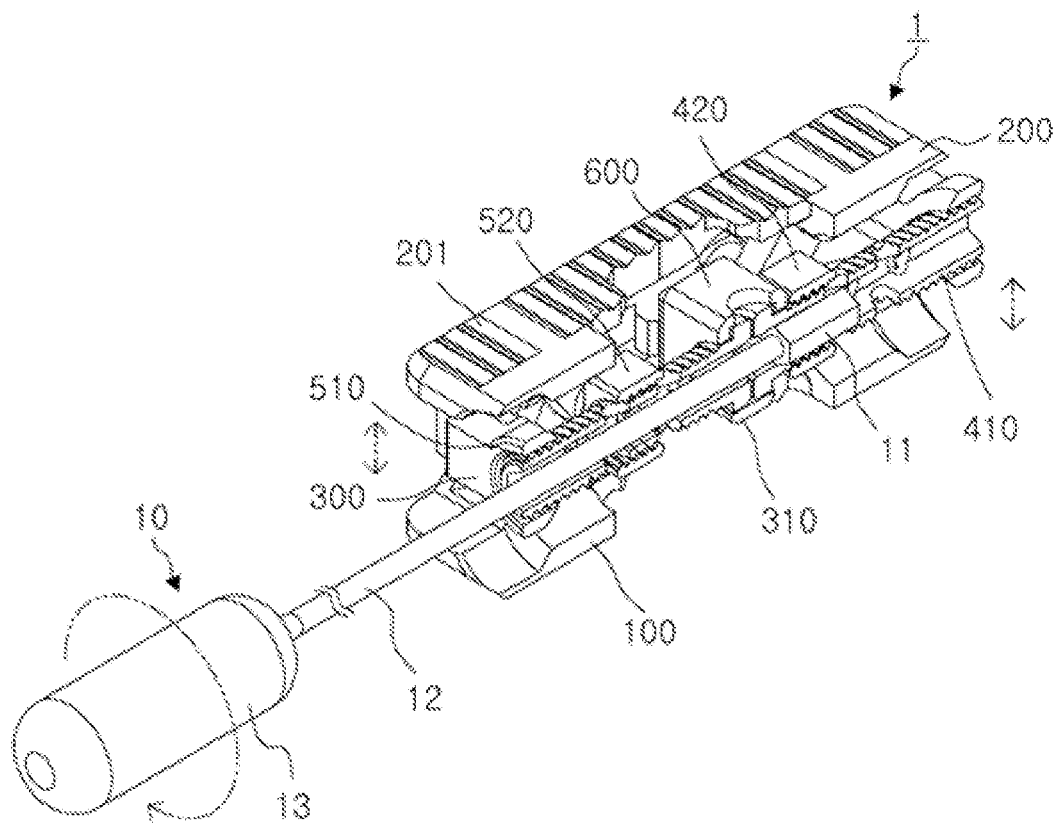
Figure 23A:
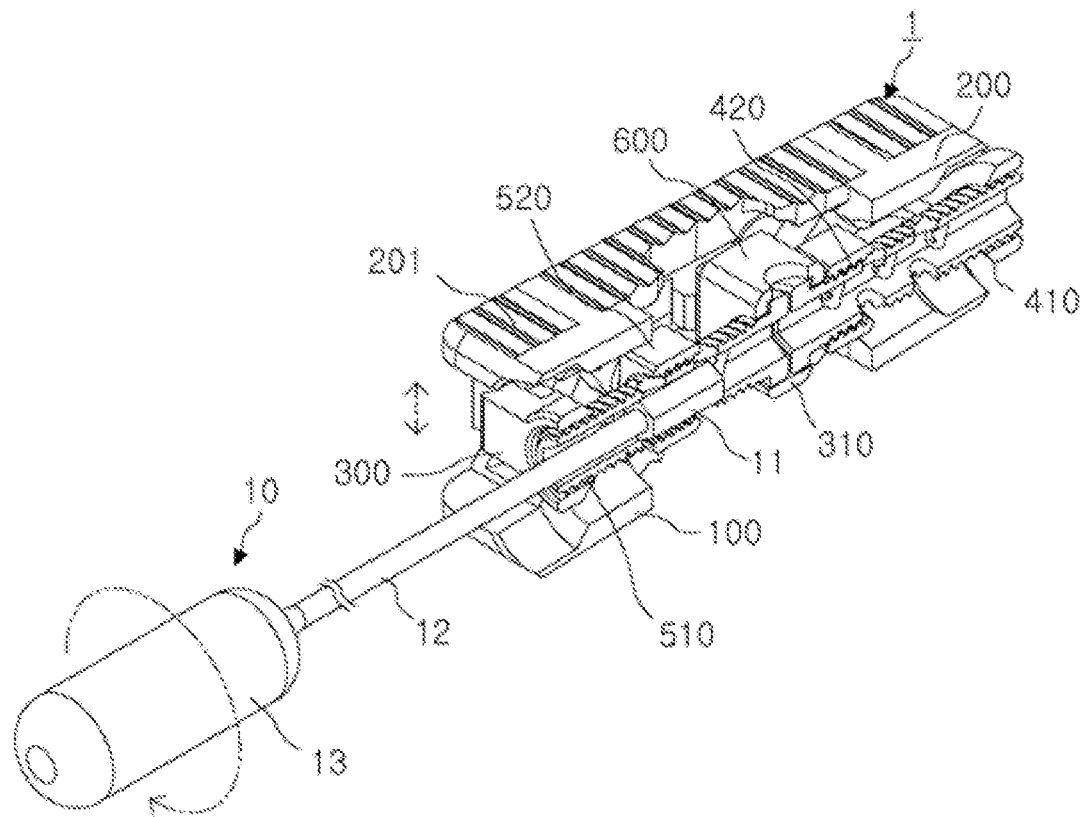
Figure 23B:
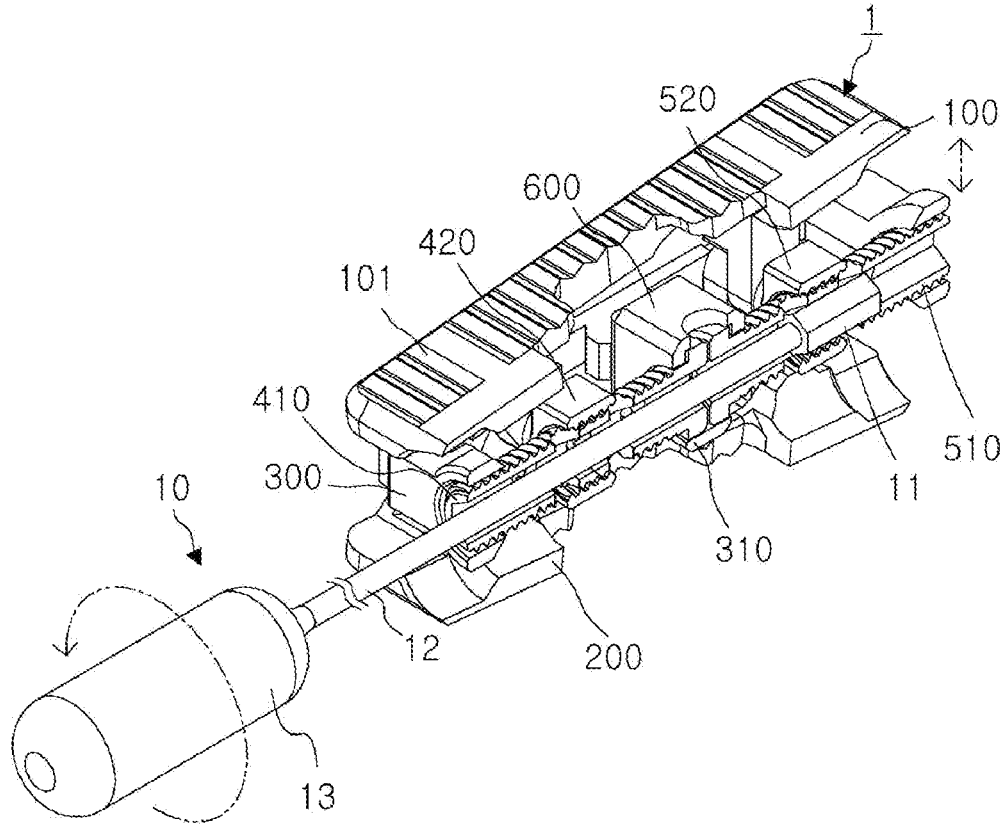

As illustrated in FIGS. 19 and 22, when the height adjusting screw 410 rotates the inclination adjusting screw 510 connected by the main frame 300 to reach the set expansion range, the user stops rotating the control mechanism 10 to complete the sagittal balance adjustment.

That is, as illustrated in FIG. 19 or 22, when the hexagonal head 11 of the control mechanism 10 rotates the height adjusting screw 410, the distance between the upper structural body 100 and lower structural body 200 is expanded through the height adjusting member 420, thereby adjusting the sagittal balance of the spine.

To correct the coronal plane deformity of the spine, the user adjusts the coronal balance by expanding one side of each of the upper structural body 100 and the lower structural body 200 relative to the coronal plane through the coronal balance control unit 500.

To rotate only the inclination adjusting screw 510, the user advances the control mechanism 10 further in the insertion direction so that the hexagonal head 11 is inserted and coupled only into the second adjusting hole 511. In this state, the user rotates the control mechanism 10 to rotate and expand the inclination adjusting screw 510 according to the set expansion range, thereby adjusting the coronal balance of the spine.

Next, a method of performing coronal and sagittal adjustment by inserting the control mechanism 10 into the coronal balance control unit 500 will be described.

In this case, unlike previously described, the user inserts the control mechanism 10 from the direction of the inclination adjusting screw 510 so that the hexagonal head 11 is inserted and coupled into both the first adjusting hole 411 of the height adjusting screw 410 and the second adjusting hole 511 of the inclination adjusting screw 510.

Thereafter, the user rotates the control mechanism 10 to rotate both the height adjusting screw 410 and the inclination adjusting screw 510 simultaneously and expand the distance between the upper structural body 100 and the lower structural body 200, thereby adjusting the sagittal balance.

To correct the coronal plane deformity of the spine, the user retracts the control mechanism 10 in the opposite direction to the insertion direction so that the hexagonal head 11 is inserted and coupled only into the second adjusting hole 511, and then rotates the control mechanism 10.

Thus, one side of the spinal expansion cage 1 can be expanded, thereby adjusting the spinal coronal balance.

According to the above, the user rotates the height adjusting screw 410 and inclination adjusting screw 510 by simply adjusting the insertion depth of the control mechanism 10, without replacement and re-insertion of the control mechanism 10 to adjust the sagittal balance and the coronal balance, thereby easily adjusting the sagittal balance and the coronal balance. In other words, the correction of sagittal and coronal deformities can be performed independently or in order as decided by the user's determination, but is not limited thereto.

Moreover, the spinal expansion cage 1 according to the present invention can be inserted in the left direction or the right direction or in both right and left directions, considering the lateral or anterolateral insertion method, and the anterior-posterior direction of the coronal balance control unit 500 with respect to the insertion direction can be changed, so, after insertion, the left or right side of the spine can be selectively expanded.

In other words, the upper level of the patient's spine to be operated on is lowered at the left side and the lower level is lowered at the right side, requiring expansion at the left side of the upper level and at the right of the lower level. In the above case, according to the present invention, after only one side is incised without the need to incise both the left and right sides, the expandable cage 1 is inserted into the incision site by being rotated to be reversed at 180 degrees around the Y-axis to correspond to the expanded position to expand the spine.

For example, if the patient's left side (or ipsilateral side) needs to be incised and the left side of the spine expanded when viewed from the front, the user aligns the anterior-posterior direction of the spinal expansion cage 1 so that the coronal balance control unit 500 is closer to the incision site and inserts the coronal balance control unit 500 into the transplantation space through the insertion tool.

On the other hand, if the patient's left side is incised and the right side of the spine needs to be expanded, the user rotates the spinal expansion cage 1 to be reversed at 180° around the Y-axis so that the coronal balance control unit 500 is located on one side far from the incision site, and then inserts the coronal balance control unit 500 into the transplantation space through the insertion tool.

As described above, the expandable cage 1 for the spine according to the present invention can selectively expand the left side or the right side of the spine by changing the direction of the sagittal balance control unit 400 and the coronal balance control unit 500 according to the patient's spinal condition, thereby adjusting the coronal balance. Since expansion of both the left and right sides of the spine is possible by incising only one side of the spine, the expandable cage 1 for the spine according to the present invention provides the effect of minimizing incision. The expandable cage 1 for the spine according to the present invention can also be operated by the anterior insertion (ALIF) or the posterior insertion (TLIF or PLIF), relieve the burden on the patient, and show excellent performance compatibility.

To summarize, the expandable cage 1 for the spine according to the present invention, which is in an unexpanded state, is inserted from the lateral or anterolateral side of the spine through the insertion tool. After the insertion, the user rotates the height adjusting screw 410 by using the control mechanism 10 to expand the distance between the upper structural body 100 and the lower structural body 200, thereby adjusting the sagittal balance by the primary expansion (horizontal expansion) of the spinal expansion cage 1. For the coronal balance, the insertion depth of the control mechanism 10 is varied to rotate the inclination adjusting screw 510 such that one side of the spinal expansion cage 1 is expanded, thereby adjusting the coronal balance by the secondary expansion of the spinal expansion cage 1.

In addition, the expansion of the sagittal plane and the expansion of the coronal plane can be performed independently, or the order of the coronal plane deformity correction and the sagittal plane deformity correction can be decided according to the user's determination, but is not limited thereto.

As described above, the expandable cage for the spine according to an embodiment of the present invention can adjust not only the sagittal balance but also the coronal balance of the spines through the sagittal balance control unit and the coronal balance control unit, thereby enabling treatment of scoliosis or kyphosis, and enabling effective treatment of complex spinal deformities with a single configuration. Moreover, the expandable cage for the spine according to an embodiment of the present invention, which is designed to be inserted from the lateral position or the anterolateral position, allows for safe surgery by minimizing the risk of damage to muscles or ligaments of the human body during surgery, and is applicable for lateral lumbar interbody fusion (LLIF) as well as antero-psoas (Anterolateral) Interbody Fusion.

Furthermore, the expandable cage for the spine according to an embodiment of the present invention is designed for a user to easily operate both the sagittal balance control unit and the coronal balance control unit through a single control mechanism, thereby facilitating the adjustment of the sagittal balance and the coronal balance. Additionally, the expandable cage for the spine according to an embodiment of the present invention has both sides symmetrically formed with respect to the longitudinal (insertion) direction, thereby allowing for easy adjustment of the expansion position in the anterior-posterior direction according to the expansion position on either the left or right side of the spine, when adjusting the coronal balance through the coronal balance control unit, and minimizing an incision area.

In addition, the expandable cage for the spine according to an embodiment of the present invention is configured to adjust the sagittal balance and the coronal balance depending on the thread pitch by rotating the height adjusting screw of the sagittal balance control unit and the inclination adjusting screw of the coronal balance control unit, thereby allowing for optimal treatment tailored to the condition of the spine through fine-tuning of expansion depending on the thread pitch, and enhancing usability only through rotation of the height adjusting screw and the inclination adjusting screw.

With reference to FIGS. 1 through 23B, the expandable cage for the spine according to an embodiment of the present invention has been described in detail, but the scope of the present invention is not limited thereto, and various modifications and improvements made by those skilled in the art using the basic concept of the present invention as defined in the following claims also fall within the scope of the invention.

The invention claimed is:

1. An expandable cage for a spine comprising:

an upper structural body;

a lower structural body spaced at a predetermined distance below the upper structural body;

a main frame disposed between the upper and lower structural bodies, and having control mechanism insertion holes defined on two sides thereof in a longitudinal direction for insertion of a control mechanism;

a sagittal balance control unit coupled to the main frame and coupled to a first side of each of the upper and lower structural bodies, the sagittal balance control unit configured to adjust a sagittal balance of the spine by adjusting a distance between the upper and lower structural bodies using the control mechanism inserted into the control mechanism insertion holes; and a coronal balance control unit coupled to the main frame and coupled to a second side of the each of the upper and lower structural bodies, the coronal balance control unit configured to adjust a coronal balance of the spine by adjusting an inclination of the upper and lower structural bodies by elevating and lowering the second sides of the upper and lower structural bodies using the control mechanism inserted into the control mechanism insertion holes, wherein the sagittal balance control unit comprises:

a height adjusting screw, disposed in the longitudinal direction of the upper and lower structural bodies, having a screw thread defined on an outer circumferential surface thereof, and configured to rotate according to a rotation of the control mechanism when the control mechanism is inserted therein;

a height adjusting member, having a screw hole coaxial with the control mechanism insertion hole, and screw-coupled with the height adjusting screw to move according to the rotation of the height adjusting screw; and a height adjusting link, having an upper end connected to the upper structural body and a lower end connected to the lower structural body, and linked with the height adjusting member to adjust a height between the upper and lower structural bodies according to a movement of the height adjusting member, wherein the height adjusting link comprises:

a fixed shaft coupled to the main frame;

a moving shaft disposed on the height adjusting member;

a first height adjusting link frame having one side rotatably coupled to the fixed shaft and another side rotatably coupled to the upper structural body;

a second height adjusting link frame having one side rotatably coupled to the fixed shaft and another side rotatably coupled to the lower structural body;

a third height adjusting link frame having one side rotatably coupled to the moving shaft and another side rotatably coupled to the upper structural body; and a fourth height adjusting link frame having one side rotatably coupled to the moving shaft and another side rotatably coupled to the lower structural body, and wherein the height adjusting link has a rhomboidal link structure and the height between the upper and lower structural bodies is adjusted by adjusting a distance between the moving shaft and the fixed shaft.

2. The expandable cage according to claim 1, wherein the coronal balance control unit comprises:

an inclination adjusting screw, arranged in the longitudinal direction of the upper and lower structural bodies, having a screw thread defined on an outer circumferential surface thereof, and configured to rotate according to the rotation of the control mechanism when the control mechanism is inserted therein;

an inclination adjusting member, having a screw hole coaxial with the control mechanism insertion hole, and screw-coupled with the inclination adjusting screw to move according to the rotation of the inclination adjusting screw; and an inclination adjusting link having one side connected to the upper structural body and another side connected to the lower structural body, and configured to adjust the inclination of the upper and lower structural bodies according to the movement of the inclination adjusting member.

3. The expandable cage according to claim 2, wherein the inclination adjusting link comprises:

a rotational shaft disposed on the inclination adjusting member;

a first inclination adjusting link frame having one side rotatably coupled to the rotational shaft and another side rotatably coupled to the upper structural body; and a second inclination adjusting link frame having one side thereof is rotatably coupled to the rotational shaft and another side rotatably coupled to the lower structural body.

4. The expandable cage according to claim 3, further comprising:

a guide member disposed to move within the main frame, wherein the guide member is configured to accommodate an end portion of the height adjusting screw and an end portion of the inclination adjusting screw, which are inserted therein in opposite directions from each other, thereby guiding both the height adjusting screw and the inclination adjusting screw.

5. The expandable cage according to claim 2, wherein the height adjusting screw comprises a first adjusting hole for the insertion of the control mechanism, the first adjusting hole having a diameter and a polygonal cross-sectional shape, and configured to be rotated according to the rotation of the control mechanism when the control mechanism is inserted therein, and wherein the inclination adjusting screw comprises a second adjusting hole for the insertion of the control mechanism, the second adjusting hole having a same diameter and cross-sectional shape as the first adjusting hole, and configured to be rotated by the rotation of the control mechanism when the control mechanism is inserted therein.

6. The expandable cage according to claim 5, wherein the height adjusting screw is aligned with the inclination adjusting screw, and the first adjusting hole and the second adjusting hole are coaxially arranged, and wherein the control mechanism is configured to rotate at least one of the height adjusting screw or the inclination adjusting screw depending on an insertion depth of the control mechanism.

7. The expandable cage according to claim 1, wherein the upper structural body comprises a first fixing force forming part disposed on an outer surface of the upper structural body and configured to face a first vertebra, and formed to protrude or to be recessed with a predetermined pattern to generate fixation force between directly contacting parts, and wherein the lower structural body comprises a second fixing force forming part disposed on an outer surface of the lower structural body and configured to face a second vertebra, and formed to protrude or to be recessed with a predetermined pattern to generate fixation force between directly contacting parts.

* * * * *